United States Patent
Popp

(10) Patent No.: US 7,680,553 B2
(45) Date of Patent: Mar. 16, 2010

(54) METHODS OF INTERFACING NANOMATERIALS FOR THE MONITORING AND EXECUTION OF PHARMACEUTICAL MANUFACTURING PROCESSES

(75) Inventor: Shane M. Popp, Santa Monica, CA (US)

(73) Assignee: SMP Logic Systems LLC, Santa Monica ( * ) Notice: Subject to any disclaimer, the term of this patent is extended or adjusted under 35 U.S.C. 154(b) by 0 days.

(21) Appl. No.: 11/715,627

(22) Filed: Mar. 8, 2007

(65) Prior Publication Data

US 2008/0221722 A1     Sep. 11, 2008

(51) Int. Cl.
  *G06F 19/00*    (2006.01)
  *G05B 21/00*   (2006.01)
(52) U.S. Cl. .................. 700/108; 700/110; 700/117; 700/266; 702/22; 977/953
(58) Field of Classification Search ......... 700/108–110, 700/117, 266; 702/19, 22; 977/708, 839, 977/953
See application file for complete search history.

(56) References Cited

U.S. PATENT DOCUMENTS

| | | | |
|---|---|---|---|
| 4,554,887 A * | 11/1985 | Yoakam et al. | 118/666 |
| 4,629,595 A | 12/1986 | Ito | |
| 4,775,439 A | 10/1988 | Seeger, Jr. et al. | |
| 4,955,993 A | 9/1990 | Sanders et al. | |
| 5,171,995 A | 12/1992 | Gast et al. | |
| 5,221,415 A | 6/1993 | Albrecht et al. | |
| 5,262,644 A | 11/1993 | Maguire | |
| 5,345,815 A | 9/1994 | Albrecht et al. | |
| 5,399,232 A | 3/1995 | Albrecht et al. | |
| 5,421,926 A | 6/1995 | Yukinobu et al. | |
| 5,483,822 A | 1/1996 | Albrecht et al. | |
| 5,580,827 A | 12/1996 | Akamine | |
| 5,595,942 A | 1/1997 | Albrecht et al. | |
| 5,662,962 A | 9/1997 | Kawata et al. | |
| 5,679,954 A | 10/1997 | Soloman | |
| 5,742,377 A | 4/1998 | Minne et al. | |
| 5,832,449 A | 11/1998 | Cunningham | |
| 5,900,634 A | 5/1999 | Soloman | |
| 6,055,507 A | 4/2000 | Cunningham | |
| 6,075,585 A | 6/2000 | Minne et al. | |
| 6,310,348 B1 | 10/2001 | Melling et al. | |
| 6,316,772 B1 | 11/2001 | Egelberg | |

(Continued)

FOREIGN PATENT DOCUMENTS

EP       0 999 506       10/2000

(Continued)

OTHER PUBLICATIONS

Off-the-Shelf Software use in Medical Devices, Guidance for Industry, United States Department of Health and Human Services, Sep. 9, 1999.

(Continued)

*Primary Examiner*—Sean P Shechtman

(57) ABSTRACT

Methods of interfacing nanomaterials used to monitor and execute the pharmaceutical manufacturing process are disclosed herein. The nanomaterials are useful to provide a plurality of analysis to the manufacturing process. Consequently, the methods provide a means to perform validation and quality manufacturing on an integrated level whereby pharmaceutical manufacturers can achieve data and product integrity and ultimately minimize cost.

12 Claims, 7 Drawing Sheets

U.S. PATENT DOCUMENTS

| | | |
|---|---|---|
| 6,395,538 B1 | 5/2002 | Naughton et al. |
| 6,450,189 B1* | 9/2002 | Ganan-Calvo ............... 137/12 |
| 6,514,453 B2 | 2/2003 | Vigliotti et al. |
| 6,522,939 B1* | 2/2003 | Strauch et al. ............. 700/116 |
| 6,573,369 B2 | 6/2003 | Henderson et al. |
| 6,635,311 B1 | 10/2003 | Mirkin et al. |
| 6,641,036 B1 | 11/2003 | Kalinowski |
| 6,642,129 B2 | 11/2003 | Liu et al. |
| 6,771,369 B2 | 8/2004 | Rzasa et al. |
| 6,777,982 B2 | 8/2004 | Goldstein et al. |
| 6,818,450 B2 | 11/2004 | Eaton et al. |
| 6,827,979 B2 | 12/2004 | Mirkin et al. |
| 6,867,443 B2 | 3/2005 | Liu et al. |
| 6,894,660 B2 | 5/2005 | Sanogo |
| 6,929,412 B1 | 8/2005 | Barrus et al. |
| 6,946,951 B2 | 9/2005 | Cole et al. |
| 6,959,248 B2 | 10/2005 | Gard et al. |
| 6,979,415 B1 | 12/2005 | Krishna et al. |
| 6,986,989 B2 | 1/2006 | Mirkin et al. |
| 6,998,228 B2 | 2/2006 | Henderson et al. |
| 7,005,378 B2 | 2/2006 | Crocker et al. |
| 7,047,792 B1 | 5/2006 | Bhethanabotla et al. |
| 7,050,875 B2 | 5/2006 | Cribbs et al. |
| 7,060,977 B1 | 6/2006 | Dupeyrat et al. |
| 7,079,912 B2 | 7/2006 | Stack et al. |
| 7,098,056 B2 | 8/2006 | Demers |
| 7,098,320 B1 | 8/2006 | Mirkin et al. |
| 7,102,656 B2 | 9/2006 | Mirkin et al. |
| 7,123,359 B2 | 10/2006 | Armstrong et al. |
| 7,125,660 B2 | 10/2006 | Stanton et al. |
| 7,135,054 B2 | 11/2006 | Jin et al. |
| 7,164,209 B1 | 1/2007 | Duan et al. |
| 7,171,312 B2 | 1/2007 | Steinthal et al. |
| 7,178,747 B2 | 2/2007 | Yadav et al. |
| 7,179,692 B2 | 2/2007 | Yu et al. |
| 7,199,305 B2 | 4/2007 | Cruchon-Dupeyrat et al. |
| 7,219,568 B2 | 5/2007 | Folestad et al. |
| 7,221,259 B2 | 5/2007 | Cole |
| 7,223,438 B2 | 5/2007 | Mirkin et al. |
| 7,267,275 B2 | 9/2007 | Cox, Jr. et al. |
| 7,276,700 B2 | 10/2007 | Abrahamson et al. |
| 7,279,046 B2 | 10/2007 | Eby et al. |
| 7,288,768 B2 | 10/2007 | Gore et al. |
| 7,361,310 B1 | 4/2008 | Mirkin et al. |
| 2002/0138510 A1 | 9/2002 | Tan |
| 2003/0038033 A1 | 2/2003 | Harker et al. |
| 2003/0068446 A1 | 4/2003 | Mirkin et al. |
| 2003/0072716 A1 | 4/2003 | Poovathinthodiyil et al. |
| 2003/0074223 A1 | 4/2003 | Hickle |
| 2003/0087239 A1 | 5/2003 | Stanton et al. |
| 2003/0162404 A1 | 8/2003 | Chang |
| 2003/0185967 A1 | 10/2003 | Eby et al. |
| 2003/0228603 A1 | 12/2003 | Cload et al. |
| 2004/0018515 A1 | 1/2004 | Diener et al. |
| 2004/0026681 A1 | 2/2004 | Cruchon-Dupeyrat et al. |
| 2004/0028694 A1 | 2/2004 | Young et al. |
| 2004/0081647 A1 | 4/2004 | Afeyan et al. |
| 2004/0081648 A1 | 4/2004 | Afeyan et al. |
| 2004/0117126 A1 | 6/2004 | Fetterman et al. |
| 2004/0142106 A1 | 7/2004 | Mirkin et al. |
| 2004/0150818 A1* | 8/2004 | Armstrong et al. ......... 356/301 |
| 2004/0175631 A1 | 9/2004 | Crocker et al. |
| 2004/0180203 A1 | 9/2004 | Yadav et al. |
| 2004/0204915 A1 | 10/2004 | Steinthal et al. |
| 2004/0219523 A1 | 11/2004 | Stanton et al. |
| 2005/0002849 A1 | 1/2005 | Mitsui et al. |
| 2005/0009206 A1 | 1/2005 | Mirkin et al. |
| 2005/0019434 A1 | 1/2005 | Duvert et al. |
| 2005/0033977 A1 | 2/2005 | Zurita et al. |
| 2005/0042753 A1 | 2/2005 | Yang et al. |
| 2005/0043894 A1 | 2/2005 | Fernandez |
| 2005/0074865 A1 | 4/2005 | Afeyan et al. |
| 2005/0142608 A1* | 6/2005 | Uchida et al. ................ 435/7.1 |
| 2005/0161210 A1 | 7/2005 | Zhong et al. |
| 2005/0172704 A1 | 8/2005 | Mirkin et al. |
| 2005/0200438 A1 | 9/2005 | Renaud et al. |
| 2005/0221072 A1 | 10/2005 | Dubrow et al. |
| 2005/0235869 A1 | 10/2005 | Cruchon-Dupeyrat et al. |
| 2005/0253502 A1 | 11/2005 | Gokturk |
| 2005/0255237 A1 | 11/2005 | Zhang et al. |
| 2005/0267611 A1 | 12/2005 | Ishigaki |
| 2005/0272885 A1 | 12/2005 | Mirkin et al. |
| 2005/0278052 A1 | 12/2005 | Bett et al. |
| 2006/0035087 A1 | 2/2006 | Yadav et al. |
| 2006/0040057 A1 | 2/2006 | Sheehan et al. |
| 2006/0041104 A1 | 2/2006 | Ait-Haddou et al. |
| 2006/0047453 A1 | 3/2006 | Reeve et al. |
| 2006/0047705 A1 | 3/2006 | Reade et al. |
| 2006/0068154 A1 | 3/2006 | Parce et al. |
| 2006/0068378 A1 | 3/2006 | Mirkin et al. |
| 2006/0078961 A1* | 4/2006 | Chiu et al. .................... 435/29 |
| 2006/0098781 A1 | 5/2006 | Bloom et al. |
| 2006/0100278 A1 | 5/2006 | Cooper et al. |
| 2006/0129259 A1 | 6/2006 | Tornquist et al. |
| 2006/0129265 A1 | 6/2006 | Ouchi |
| 2006/0155410 A1 | 7/2006 | Yamartino |
| 2006/0167579 A1 | 7/2006 | Fujii et al. |
| 2006/0172318 A1 | 8/2006 | Medinz et al. |
| 2006/0178841 A1 | 8/2006 | Fernandez |
| 2006/0204738 A1 | 9/2006 | Dubrow et al. |
| 2006/0232375 A1 | 10/2006 | Loussert et al. |
| 2006/0234519 A1 | 10/2006 | Pan |
| 2006/0253259 A1 | 11/2006 | Fernandez |
| 2006/0275281 A1 | 12/2006 | Sullivan |
| 2006/0275371 A1 | 12/2006 | Dai et al. |
| 2007/0019789 A1 | 1/2007 | Bloom |
| 2007/0021929 A1* | 1/2007 | Lemmo et al. ................ 702/22 |
| 2007/0027566 A1* | 2/2007 | Weder ....................... 700/110 |
| 2007/0032091 A1 | 2/2007 | Heald et al. |
| 2007/0034833 A1 | 2/2007 | Parce et al. |
| 2007/0038307 A1 | 2/2007 | McKenzie et al. |
| 2007/0099823 A1 | 5/2007 | Tarasenka et al. |
| 2007/0106333 A1 | 5/2007 | Fernandez |
| 2007/0108056 A1 | 5/2007 | Nyberg et al. |
| 2007/0141163 A1* | 6/2007 | Vitaliano et al. ............. 424/490 |
| 2007/0155021 A1 | 7/2007 | Zhang et al. |
| 2007/0156211 A1 | 7/2007 | Ferren et al. |
| 2007/0207060 A1 | 9/2007 | Zou et al. |
| 2007/0275230 A1 | 11/2007 | Murphy et al. |
| 2007/0298253 A1 | 12/2007 | Hata et al. |

FOREIGN PATENT DOCUMENTS

| | | |
|---|---|---|
| EP | 1435262 A1 | 7/2004 |
| GB | 2405203 A | 2/2005 |
| WO | WO02/22882 A2 | 3/2002 |
| WO | WO03/000192 A2 | 1/2003 |
| WO | WO03/022999 A2 | 3/2003 |
| WO | WO 03/049275 A1 | 6/2003 |
| WO | WO04/001019 A2 | 12/2003 |
| WO | WO2004/019878 A2 | 3/2004 |
| WO | WO2005/054303 A2 | 6/2005 |
| WO | WO2005/058472 A2 | 6/2005 |
| WO | WO2005/085430 A2 | 9/2005 |
| WO | WO2006/050183 A2 | 5/2006 |
| WO | WO2006/121868 A2 | 11/2006 |
| WO | WO2006/138263 A2 | 12/2006 |
| WO | WO2007/001962 A2 | 1/2007 |
| WO | WO2007/044609 A1 | 4/2007 |
| WO | WO2007/078304 A2 | 7/2007 |
| WO | WO2007/089564 A2 | 8/2007 |
| WO | WO2007/090096 A2 | 8/2007 |
| WO | WO2007/094870 A2 | 8/2007 |
| WO | WO2007/106415 A2 | 9/2007 |

WO WO2007/122651 A1 11/2007

OTHER PUBLICATIONS

Towards Supramolecular Electronics, Schenning, et. al., Synthetic Metals 147 (2004) 43-48.

Material Marriage in Electronics, Meijer, et. al., Nature, vol. 419 353-354, Sep. 26, 2002.

SAX: Solution Atomization and SonoXrystallization; Technology for Manufacture of Micro and Nano-crystalline Drug Particles, Ruecroft, et. al., pp. 1-27, 2006.

Journal of Pharmaceutical Innovation, From R&D to Market, pp. 1-84, vol. Issue 1, Sep./Oct. 2006.

IMPLUSE—Adopting a New Processing Paradigm in Chemical and Pharmaceutical Industry, Sharratt, et. al., Chem. Micro. Process Eng. Jan. 2007, pp. 33-47.

Emerging Issues in Nanoparticle Aerosol Science and Technology (NAST), NSF Workshop Report, pp. 1-119, Friedlander, et. al., Jun. 27-28, 2003.

Nanoparticles: An Occupational Hygiene Review, Institute of Occupational Health, pp. 1-113, Aitken, et. al., 2004.

Carbon Nanotube Manufacturing 2006: Introduction and Overview, Carbon Nanotube Manufacturing Workshop, National Science Foundation, Peter Eklund, p. 1-14 (Nov. 3, 2006).

Carbon Nanotube (CNT) Ordered Arrays and Directional Growth of Single CNT, Carbon Nanotube Manufacturing Workshop, National Science Foundation, Rao, p. 1-12, (Nov. 3, 2006).

World Technology Evaluation Center (WTEC), International R&D of Carbon Nanotube Manufacturing and Apps., Full Proceeding, NSF, p. 1-91, (Nov. 3, 2006).

Post Processing #1, Dispersion, Functionalization and CNT Blends, WTEC Workshop, Columbia Chemicals Co., Pradhan, p. 1-10, (Nov. 3, 2006).

* cited by examiner

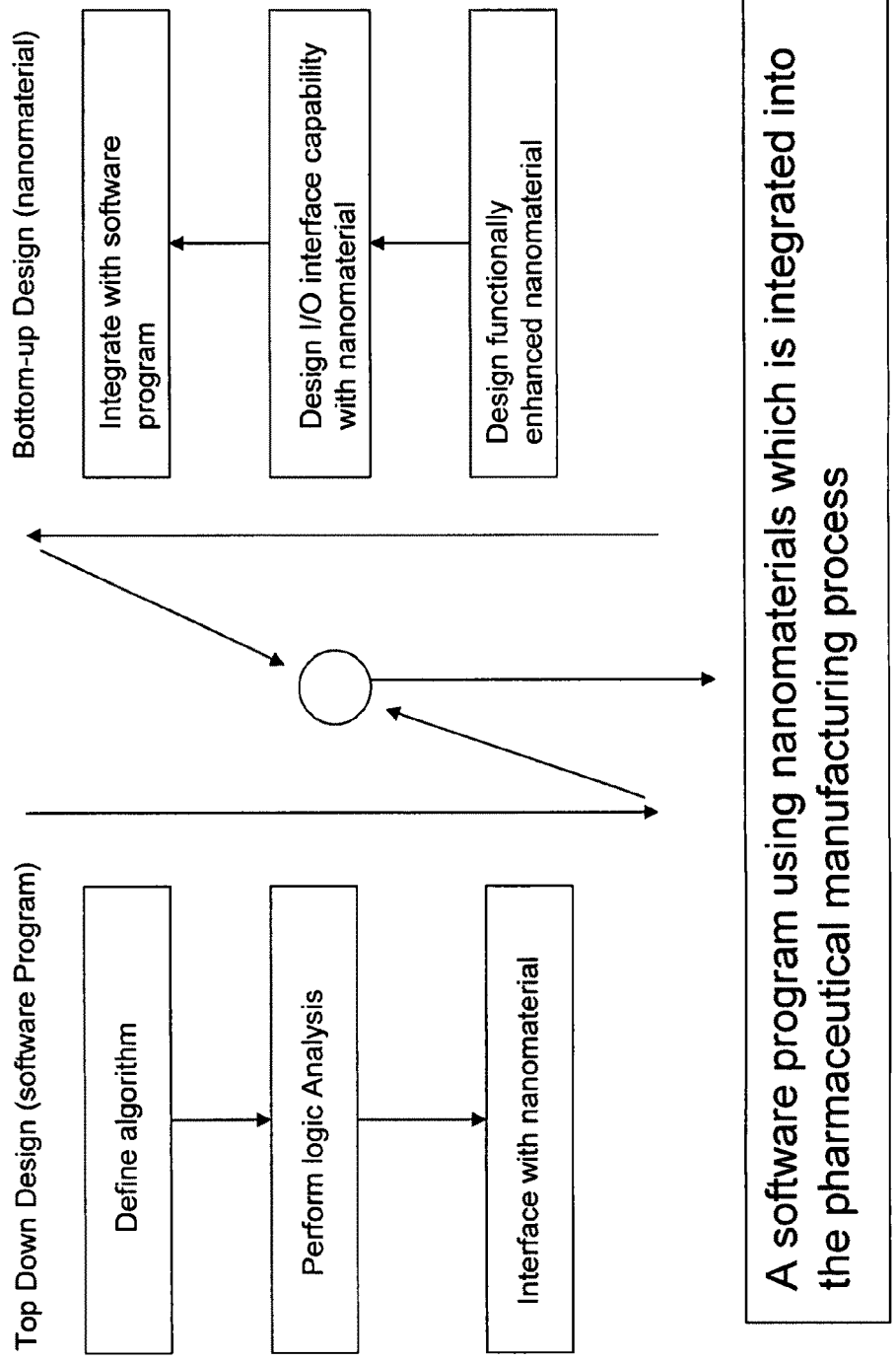
Figure 1: Hybrid Approach to interfacing nanomaterials and software programs

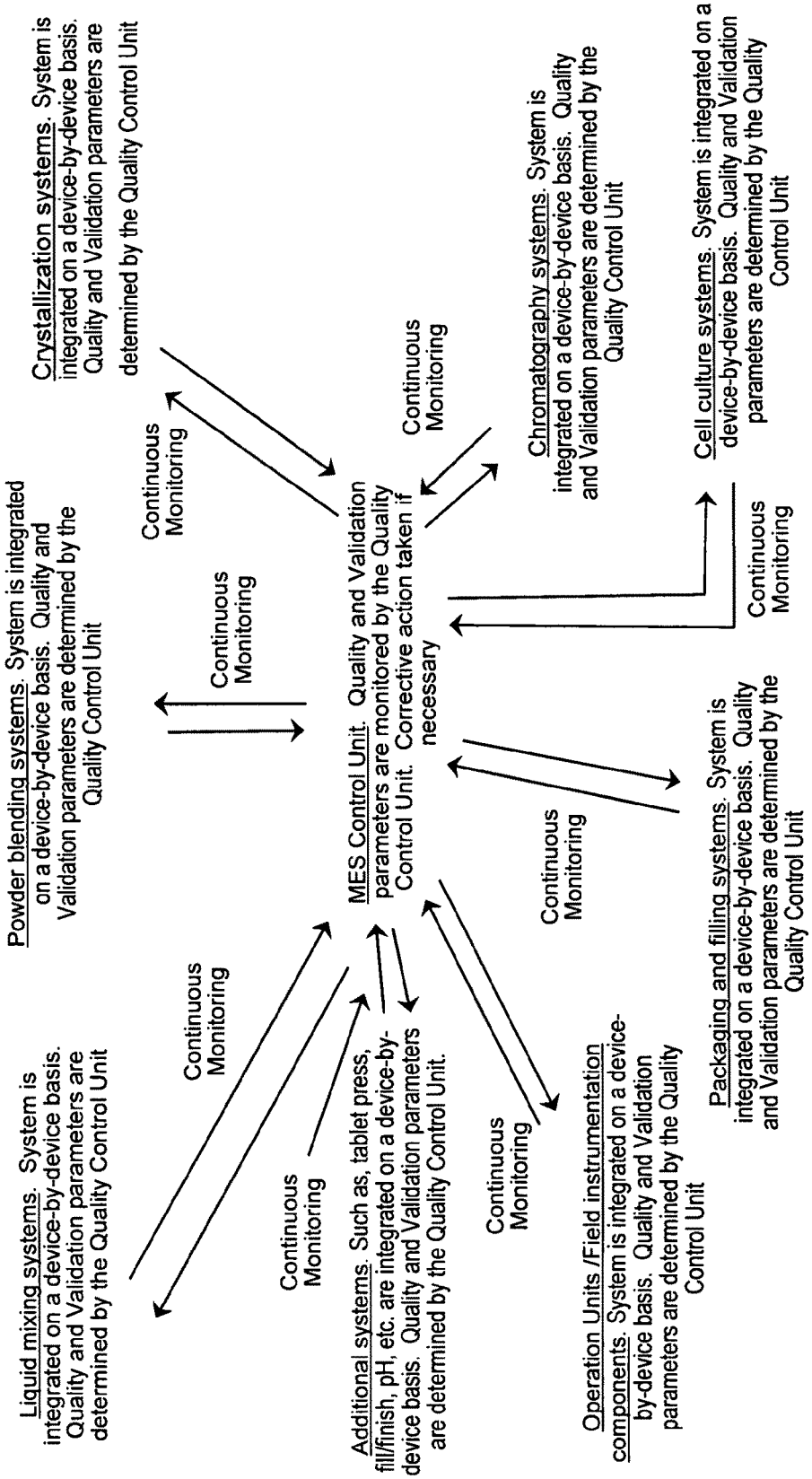
Figure 2: Schematic of Manufacturing Execution System Integration

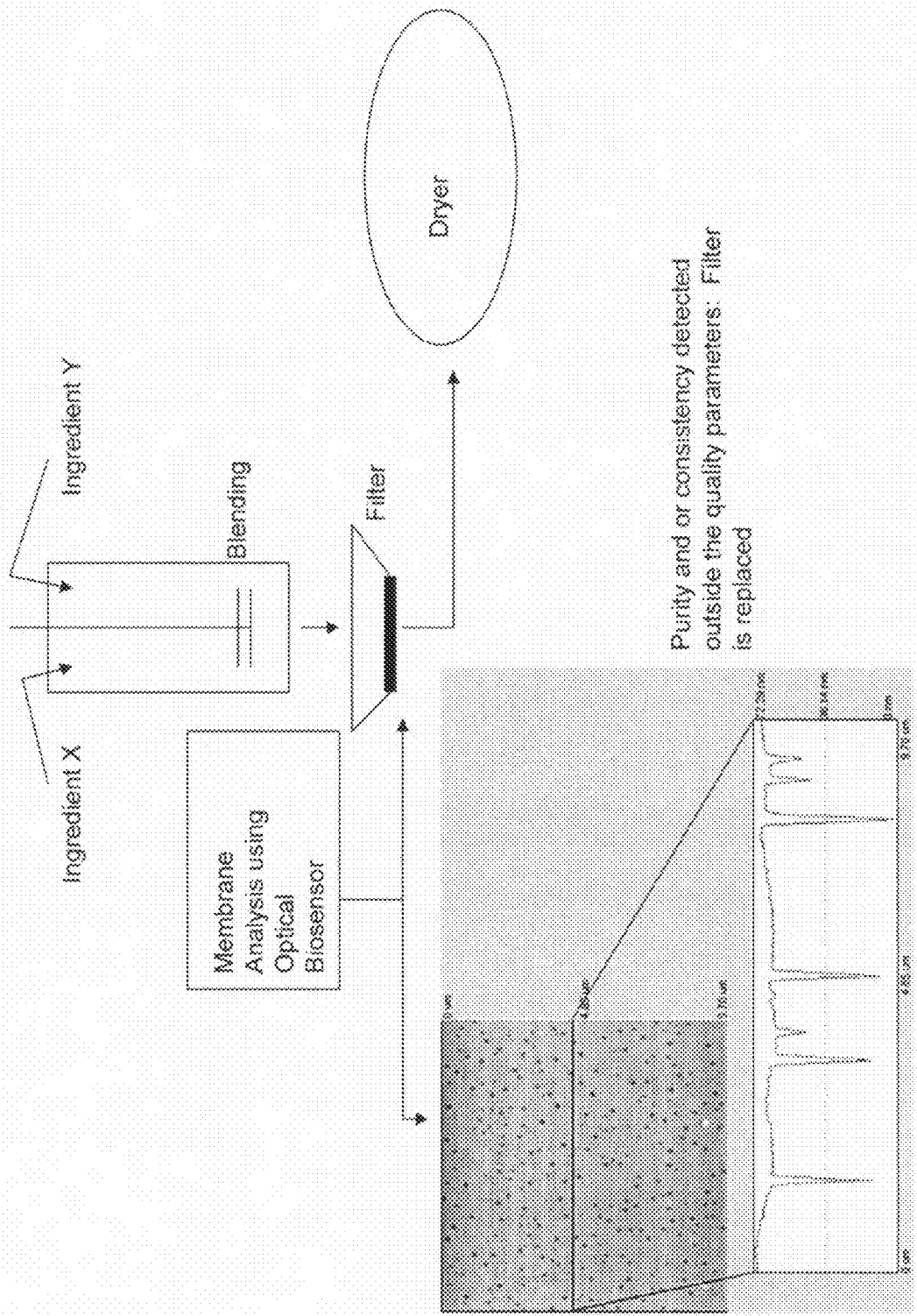
Figure 3: Membrane Analysis on Crystallization Process Using software interfaced with optical Biosensor

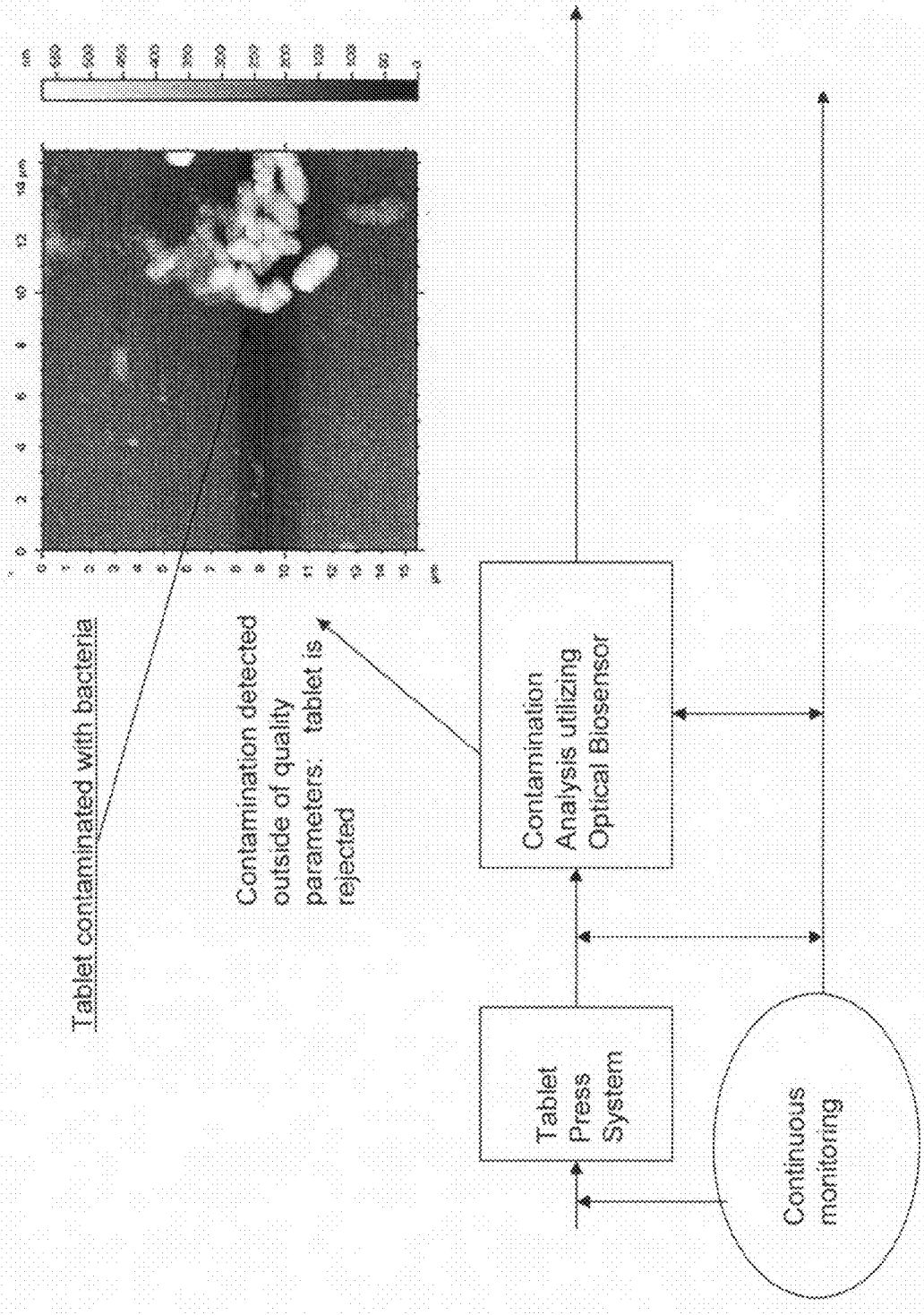
Figure 4: Contamination Analysis of Tablet Press Systems Using Software Interfaced with Optical Biosensor

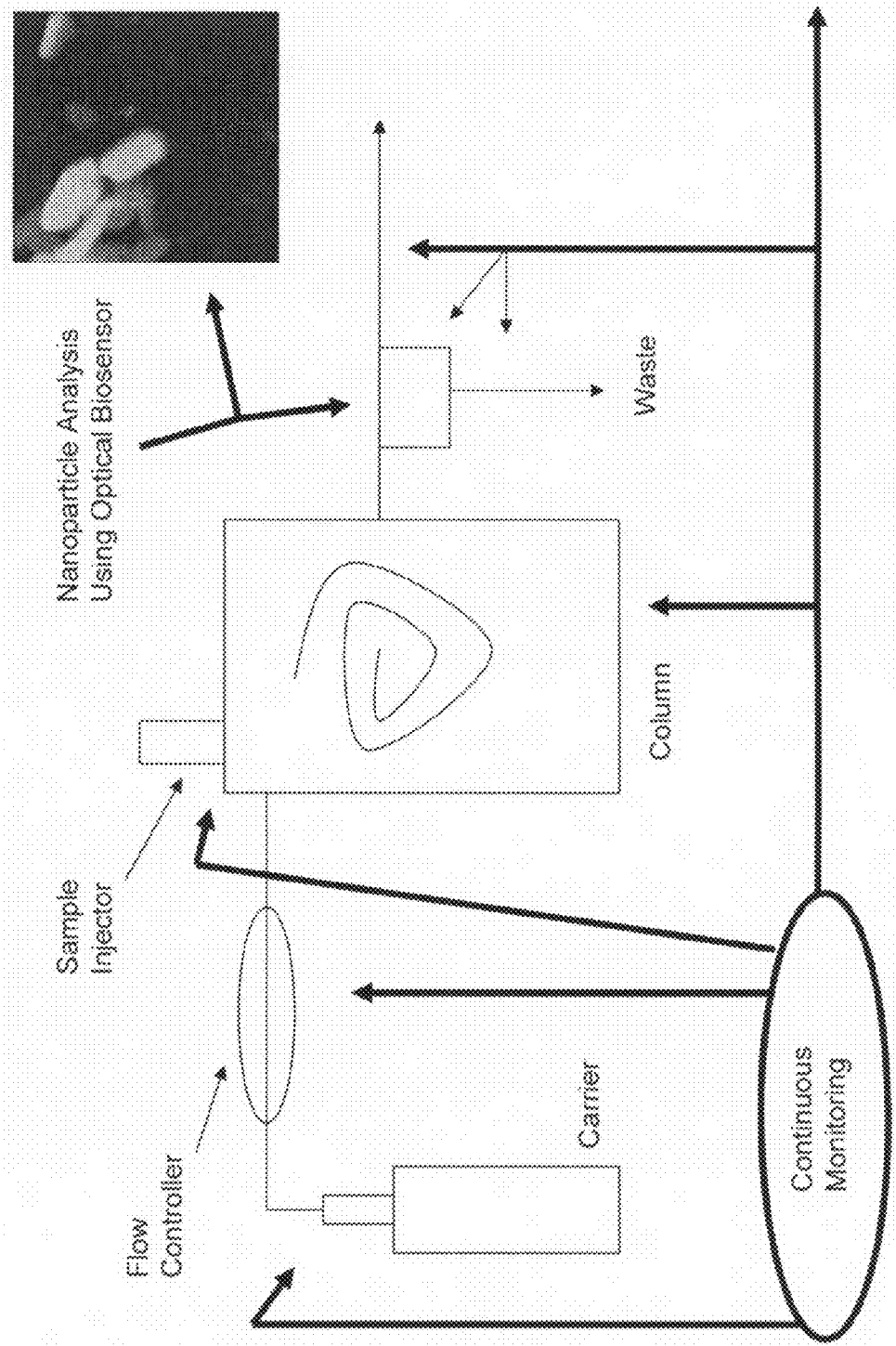

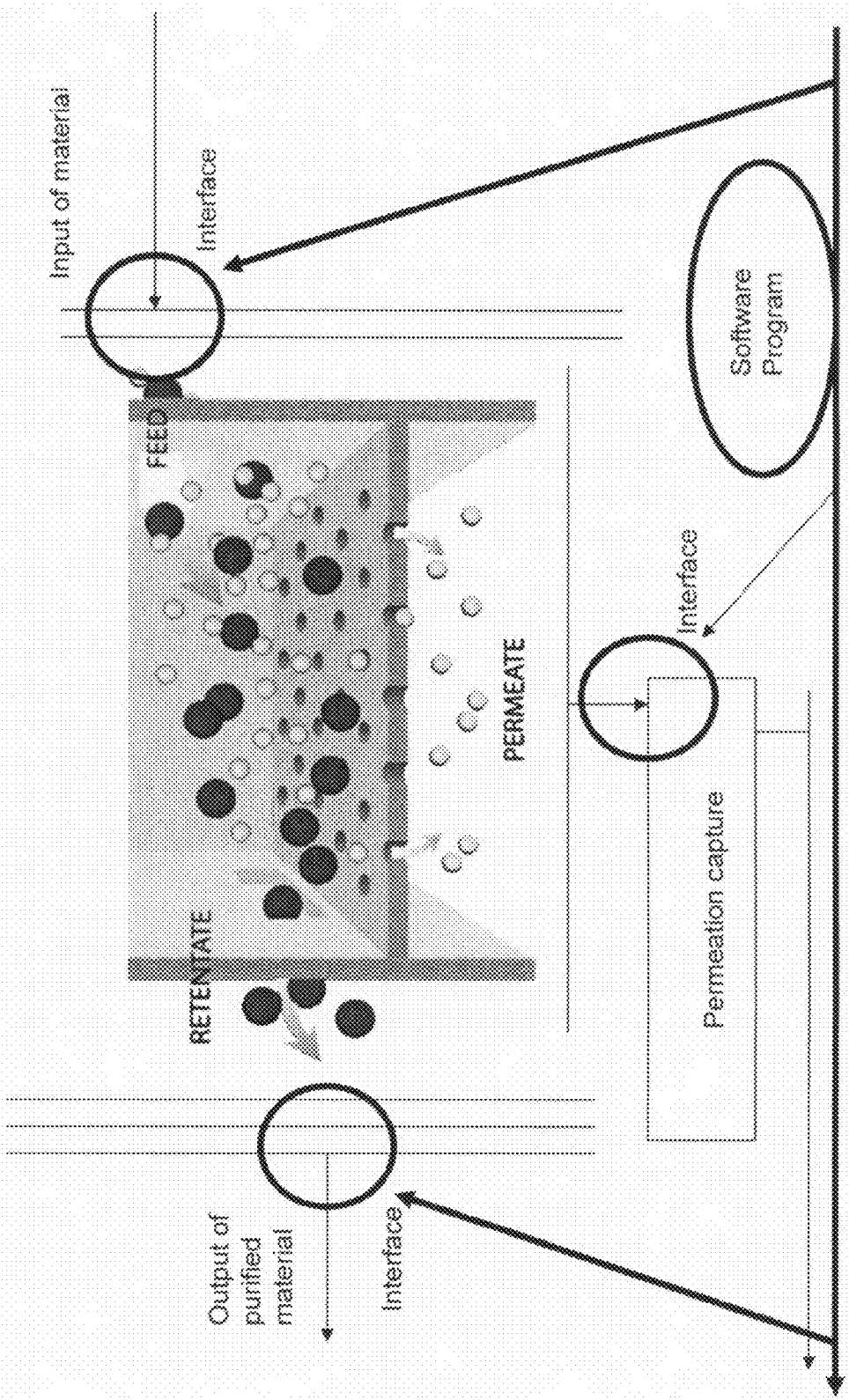
Figure 6: Nanomaterial used in filtration / purification process to separate materials in pharmaceutical manufacturing process

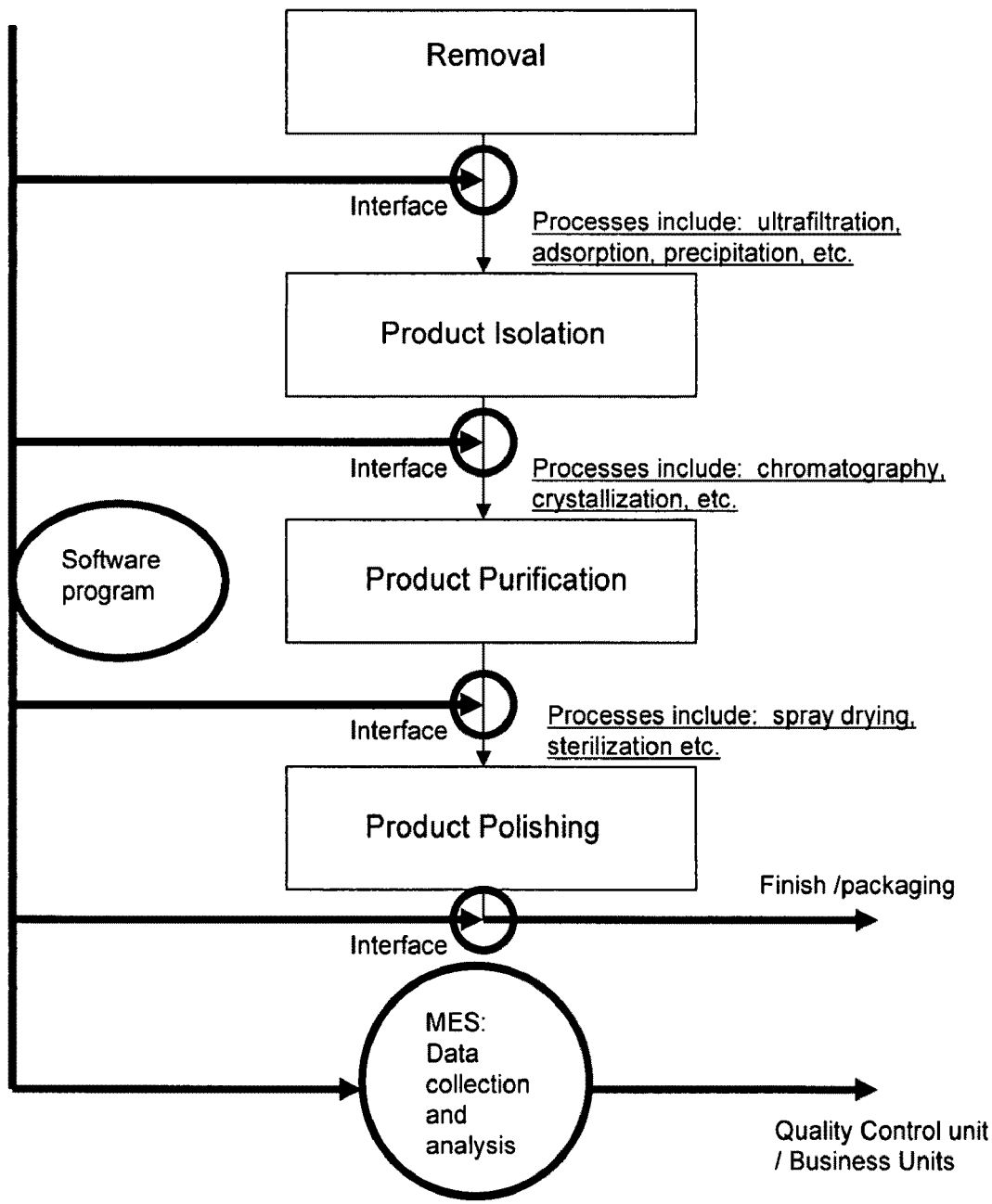
Figure 7: Interfacing nanomaterial into a downstream processing system

METHODS OF INTERFACING NANOMATERIALS FOR THE MONITORING AND EXECUTION OF PHARMACEUTICAL MANUFACTURING PROCESSES

CROSS-REFERENCE TO RELATED APPLICATIONS

Not applicable.

STATEMENT OF RIGHTS TO INVENTIONS MADE UNDER FEDERALLY SPONSORED RESEARCH

Not applicable.

FIELD OF THE INVENTION

The invention described herein relates to the field of pharmaceutical manufacturing and nanotechnologies. Specifically, methods of interfacing nanomaterials with software programs used for the monitoring and execution of pharmaceutical manufacturing processes. The invention further relates to the enhancement of nanotechnologies to produce higher quality more efficient drugs.

BACKGROUND OF THE INVENTION

Previously we have described novel methods, systems, software programs, and manufacturing execution systems for validation, quality and risk assessment, and monitoring of pharmaceutical manufacturing processes. See, US2005/0251278 published 10 Nov. 2005; US2006/0276923 published 7 Dec. 2006; US2006/0271227 Published 30 Nov. 2006; US2007/0021856 Published 25 Jan. 2007; and US2007/0032897 Published 8 Feb. 2007. Additionally, we endeavor to further the state of the art using software and computer programming in the field of nanotechnology and supramolecular electronics.

Nanotechnology is a field of applied science and technology covering a broad range of topics. The main unifying theme is the control of matter on a scale smaller than one micrometer as well as the fabrication of devices on this same length scale. Worldwide research is currently being conducted in countess areas to discover new and useful areas where nanotechnology can be exploited commercially. The research involves potential utility in industrial applications, such as pharmaceutical manufacturing as well as other areas of medicine and bioenergy just to name a few.

Despite the apparent simplicity of this definition, nanotechnology actually encompasses diverse lines of inquiry. Nanotechnology cuts across many disciplines, including colloidal science, chemistry, applied physics, biology. It could variously be seen as an extension of existing sciences into the nanoscale, or as a recasting of existing sciences using a newer, more modern term.

Two main approaches are used in nanotechnology. One is a "bottom-up" approach where materials and devices are built from molecular components which assemble themselves chemically using principles of molecular recognition. The other being a "top-down" approach where nano-objects are constructed from larger entities without atomic-level control. Nanomaterials are materials having unique properties arising from their nanoscale dimensions. The use of nanoscale materials can also be used for bulk applications. In fact, most present commercial applications of nanotechnology are of this flavor.

Nanomaterials from a "top-down" design have certain scaling deficiencies which must be assessed. For example, A number of physical phenomena become noticeably pronounced as the size of the system decreases. These include statistical mechanical effects, as well as quantum mechanical effects, for example the "quantum size effect" where the electronic properties of solids are altered with great reductions in particle size. This effect does not come into play by going from macro to micro dimensions. However, it becomes dominant when the nanometer size range is reached. Additionally, a number of physical properties change when compared to macroscopic systems. One example is the increase in surface area to volume of materials. This catalytic activity also opens potential risks in their interaction with biomaterials.

Additionally, materials reduced to the nanoscale can suddenly show very different properties compared to what they exhibit on a macroscale, enabling unique applications. For instance, opaque substances become transparent (copper); inert materials become catalysts (platinum); stable materials turn combustible (aluminum); solids turn into liquids at room temperature (gold); insulators become conductors (silicon) to name a few.

Additionally, nanosize powder particles are important for the achievement of uniform nanoporosity and similar applications. However, the tendency of small particles to form clumps ("agglomerates") is a serious technological problem that impedes such applications.

Another deficiency is that the volume of an object decreases as the third power of its linear dimensions, but the surface area only decreases as its second power. This somewhat subtle and unavoidable principle has huge ramifications. For example the power of a drill (or any other machine) is proportional to the volume, while the friction of the drill's bearings and gears is proportional to their surface area. For a normal-sized drill, the power of the device is enough to handily overcome any friction. However, scaling its length down by a factor of 1000, for example, decreases its power by $1000^3$ (a factor of a billion) while reducing the friction by only $1000^2$ (a factor of "only" a million). Proportionally it has 1000 times less power per unit friction than the original drill. If the original friction-to-power ratio was, say, 1%, that implies the smaller drill will have 10 times as much friction as power. The drill is useless.

This is why, while super-miniature electronic integrated circuits can be made to function, the same technology cannot be used to make functional mechanical devices in miniature.

Nanomaterials from a "bottom-up" design also have certain deficiencies which must be assessed. Modem synthetic chemistry has reached the point where it is possible to prepare small molecules to almost any structure. These methods are used today to produce a wide variety of useful chemicals such as pharmaceuticals or commercial polymers. However, the ability of this to extend into supramolecular assemblies consisting of many molecules arranged in a well defined manner is problematic. Such bottom-up approaches should, broadly speaking, be able to produce devices in parallel and much cheaper than top-down methods. However, most useful structures require complex and thermodynamically unlikely arrangements of atoms. The basic laws of probability and entropy make it very unlikely that atoms will "self-assemble" in useful configurations, or can be easily and economically nudged to do so. About the only example of this is crystal-growing, for which Nanotechnology cannot take any credit.

Given the deficiencies associated with "top-down" and "bottom-up" nanomaterials, it becomes clear that providing a functional approach to nanotechnology (i.e. the development of nanomaterials of a desired functionality) can be problematic. Finally, implementing nanotechnologies in highly-regulated bulk manufacturing applications, such as pharmaceutical manufacturing, only compounds problems. The present invention overcomes these problems.

SUMMARY OF THE INVENTION

The invention provides for nanomaterials with functional characteristics that can be interfaced with software programs designed for use in the pharmaceutical manufacturing process. Specifically, software programs that monitor quality control and the quality process used in the manufacture, processing, and storing of drugs. As used herein, the term "drug" is synonymous with "pharmaceutical". In certain embodiments, the nanomaterial is used in membrane analysis to ensure purity and consistency of an ingredient used in a pharmaceutical manufacturing process.

The invention further comprises a nanomaterial that is used to analyze surface derivations on pharmaceuticals and biosensors used in the pharmaceutical manufacturing process.

In certain embodiments, the nanomaterial is used in tribotechnical analysis to characterize friction, lubrication, and wearing effects on materials as a result of a pharmaceutical manufacturing process.

In certain embodiments, the nanomaterial is used in morphology analysis to characterize texture and/or roughness effects of materials as a result of a pharmaceutical manufacturing process.

In certain embodiments, the nanomaterial is used in analysis of mechanical properties to characterize hardness, elasticity, and/or compressibility properties of materials as a result of a pharmaceutical manufacturing process.

In certain embodiments, the nanomaterial is used in porosity analysis of materials as a result of a pharmaceutical manufacturing process.

In certain embodiments, the nanomaterial is used in permeability analysis of materials as a result of a pharmaceutical manufacturing process.

In certain embodiments, the nanomaterial is used in absorption analysis of materials as a result of a pharmaceutical manufacturing process.

In certain embodiments, the nanomaterial is used in purification analysis of materials as a result of a pharmaceutical manufacturing process.

In certain embodiments, the nanomaterial is used in the visualization analysis of materials as a result of a pharmaceutical manufacturing process.

Based on the foregoing non-limiting exemplary embodiments, the software program can be interfaced with the nanomaterial to monitor quality assurance protocols put in place by the quality control unit.

The invention further provides interfacing a software program with a functional nanomaterial whereby the nanomaterial is useful in measuring manufacturing parameters used in pharmaceutical manufacture.

The invention further comprises a nanomaterial system which integrates application software and methods disclosed herein to provide a comprehensive validation and quality assurance protocol that is used by a plurality of end users whereby the data compiled from the system is analyzed and used to determine is quality assurance protocols and validation protocols are being achieved.

The invention further comprises implementing the nanomaterial and software program to multiple product lines whereby simultaneous production lines are monitored using the same system.

The invention further comprises implementation of the nanomaterial and software program described herein into the crystallization process, the tablet press process, the chromatography process, the pH monitoring process, the liquid mixing process, the powder blending process, the water-for-injection systems, the water purification systems, the cell culture systems, and the finishing and packaging systems subset of the pharmaceutical manufacturing process whereby the data compiled by the subset processes is tracked continuously overtime and said data is used to analyze the subset processes and whereby said data is integrated and used to analyze the quality control process of the pharmaceutical manufacturing process at-large.

The invention further comprises a manufacturing execution system, which controls the pharmaceutical manufacturing process and increases productivity and improves quality of pharmaceuticals by interfacing the software program with a nanomaterial.

BRIEF DESCRIPTION OF THE FIGURES

FIG. 1. Schematic of a hybrid approach to interfacing nanomaterials to software programs. As shown in the figure, the left side shows a software program that is designed with a top-down design. The right side shows a nanomaterial that is designed with a bottom-up design. The software program and nanomaterials are interfaced to operate on the electrical level like conventional computing devices. The interfaced nanomaterials are then integrated into the pharmaceutical manufacturing process.

FIG. 2. Schematic of manufacturing execution system. As shown in FIG. 4, each process in the pharmaceutical manufacturing system is integrated with a computer product and data is monitored assessing various factors, the parameters of which are set forth by the quality control unit. The specific systems are then cumulatively integrated by the quality control unit and a data record is made. The data record is maintained and used to determine risk factors and make quality assessments.

FIG. 3. Membrane analysis performed on a crystallization process used in pharmaceutical manufacturing. Ingredient X is blended with ingredient Y and filtered. The nanomaterial is scanned across the filtration membrane on a continuous basis. The quality parameters for the membrane are determined by the quality control unit. The membrane analysis detects a membrane failure. The membrane is replaced.

FIG. 4. Surface deviation analysis on a tablet press process used in pharmaceutical manufacturing. Tablets are manufactured and are continuously monitored. Nanomaterials scan the surface of the tablets for surface deviations associated with the tablet press process. The quality parameters are determined by a quality control unit. Upon the detection of a deviation outside the scope of the quality parameters, a failure analysis occurs. Corrective action is taken and the defective tablets are taken out of the manufacturing process.

FIG. 5. Schematic of a chromatography system whereby the nanomaterial provides a tribo-technical analysis of an active ingredient used to manufacture pharmaceuticals. Nanomaterials scan the surface of the materials to assess morphology, roughness, or characterization associated with the chromatography process. The quality parameters are determined by a quality control unit. Upon the detection of a deviation outside the scope of the quality parameters, a failure analysis occurs. Corrective action is taken and the defective materials are taken out of the manufacturing process.

FIG. 6. Schematic of a filtration/purification process interfaced with nanomaterial. Material is fed through the input and filtered/purified. Nanomaterials monitor the materials for conformance with quality parameters. The quality parameters are determined by a quality control unit. Upon the detection of a deviation outside the scope of the quality parameters, a failure analysis occurs. Corrective action is taken and the defective materials are taken out of the manufacturing process.

FIG. 7. Schematic of a nanomaterial interfaced with a downstream processing system used in pharmaceutical manufacturing. The nanomaterial is interfaced with the Removal step, the product isolation step, the product purification step, and the product polishing step. The data is monitored and collected for conformance with quality parameters. The quality parameters are determined by a quality control unit. Upon the detection of a deviation outside the scope of the quality parameters, a failure analysis occurs. Corrective action is taken and the defective materials are taken out of the manufacturing process.

DETAILED DESCRIPTION OF THE INVENTION

Outline of Sections

I.) Definitions
II.) Nanomaterial
  a. Functional Properties of Nanomaterial
    i. Nanomaterial with thermal Conductivity
    ii. Nanomaterial with Porosity/Permeability
    iii. Nanomaterial with enhanced luminescence
    iv. Nanomaterial with enhanced acoustics
    v. Nanomaterial with magnetic properties
    vi. Nanomaterial with enhanced solubility
    vii. Shape Engineered nanomaterials
    viii. Nanomaterials with enhanced optical properties
III.) Sensors
IV.) Software Program and Computer Product
V.) Analysis
VI.) Manufacturing Execution System ("MES")
VII.) KITS/Articles of Manufacture

I.) DEFINITIONS

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized current Good Manufacturing Practice guidelines.

As used herein the terms "drug" and "pharmaceutical" include veterinary drugs and human drugs, including human biological drug products.

"Nanomaterial" means a material in any dimensional form (zero, one, two, three) and domain size less than 100 nanometers.

"Nanostructure" means a structure having at least one dimension that is less than 500 nanometers. Examples, include but are not limited to nanocrystals, nanocomposites, nanograins, nanotubes, nanoceramics, and nanopowders.

"nanocrystal" means nanostructures that are substantially monocrystalline. A nanocrystal has at least one region or characteristic dimension with a dimension of less than about 500 nm, and down to on the order of less than about 1 nm. As used herein, when referring to any numerical value, "about" means a value of .+−0.10% of the stated value (e.g. about 100 nm encompasses a range of sizes from 90 nm to 110 nm, inclusive). The terms "nanocrystal," "nanodot," "dot" and "quantum dot" are readily understood by the ordinarily skilled artisan to represent like structures and are used herein interchangeably. The present invention also encompasses the use of polycrystalline or amorphous nanocrystals.

"aspect ratio" means the ratio of the maximum to the minimum dimension of a particle.

"biomaterial" (a.k.a. biological material) may refer to biological matter, biomass, biomolecule, and organic material (i.e. derived from living things or containing carbon).

"Integrated circuits (IC)" means a miniaturized electronic circuit that has been manufactured in the surface of a thin substrate of semiconductor material.

"hybrid integrated circuit" means a miniaturized electronic circuit bonded to a substrate or circuit board.

"nanowire" means a wire of dimensions of the order of a nanometer ($10^{-9}$ meters). Alternatively, nanowires can be defined as structures that have a lateral size constrained to tens of nanometers or less and an unconstrained longitudinal size. Nanowires include metallic (e.g., Ni, Pt, Au), semiconducting (e.g., InP, Si, GaN, etc.), and insulating (e.g., $SiO_2$, $TiO_2$). Molecular nanowires are composed of repeating molecular units either organic (e.g. DNA) or inorganic (e.g. $Mo_6S_{9-x}I_x$).

"domain size" means the minimum dimension of a particular material morphology. In the case of powders, the domain size is the grain size. In the case of whiskers and fibers, the domain size is the diameter. In the case of plates and films, the domain size is the thickness.

"nanopowder" (a.k.a. "nanosize powders," "nanoparticles," and "nanoscale powders") means and refer to fine powders that have a mean size less than 250 nanometers. For example, in some embodiments, the nanopowders are powders that have particles with a mean domain size less than 100 nanometers and with an aspect ratio ranging from 1 to 1,000,000. Pure powders, as the term used herein, are powders that have composition purity of at least 99.9% by metal basis. For example, in some embodiments the preferred purity is 99.99%.

"Powder" (a.k.a. "powder", "particle", and "grain") are used interchangeably and encompass oxides, carbides, nitrides, borides, chalcogenides, halides, metals, intermetallics, ceramics, polymers, alloys, and combinations thereof. These terms include single metal, multi-metal, and complex compositions. These terms further include hollow, dense, porous, semi-porous, coated, uncoated, layered, laminated, simple, complex, dendritic, inorganic, organic, elemental, non-elemental, composite, doped, undoped, spherical, non-spherical, surface functionalized, surface non-functionalized, stoichiometric, and non-stoichiometric forms or substances. Further, the term powder in its generic sense includes one-dimensional materials (fibers, tubes, etc.), two-dimensional materials (platelets, films, laminates, planar, etc.), and three-dimensional materials (spheres, cones, ovals, cylindrical, cubes, monoclinic, parallelolipids, dumbbells, hexagonal, truncated dodecahedron, irregular shaped structures, etc.). The term metal used above includes any alkali metal, alkaline earth metal, rare earth metal, transition metal, semi-metal (metalloids), precious metal, heavy metal, radioactive metal, isotopes, amphoteric element, electropositive element, cation forming element, and includes any current or future discovered element in the periodic table.

"Precursor" means any raw substance that can be transformed into a powder of same or different composition. In certain embodiments, the precursor is a liquid. The term precursor includes, but is not limited to, organometallics, organics, inorganics, solutions, dispersions, melts, sols, gels, emulsions, or mixtures.

"nanofiller" (a.k.a. nanostructured filler) means a structure or particle intimately mixed with a matrix to form a nanostructured composite. At least one of the nanostructured filler and the nanostructured composite has a desired material property which differs by at least 20% from the same material property for a micron-scale filler or a micron-scale composite, respectively. The desired material property is selected from the group consisting of refractive index, transparency to light, reflection characteristics, resistivity, permittivity, permeability, coercivity, B-H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility and wear rate. The nanostructured filler may comprise one or more elements selected from the s, p, d, and f groups of the periodic table, or it may comprise a compound of one or more such elements with one or more suitable anions, such as aluminum, antimony, boron, bromine, carbon, chlorine, fluorine, germanium, hydrogen, indium, iodine, nickel, nitrogen, oxygen, phosphorus, selenium, silicon, sulfur, or tellurium. The matrix may be a polymer (e.g., poly(methyl methacrylate), poly(vinyl alcohol), polycarbonate, polyalkene, or polyaryl), a ceramic (e.g., zinc oxide, indium-tin oxide, hafnium carbide, or ferrite), or a metal (e.g., copper, tin, zinc, or iron). Loadings of the nanofiller may be as high as 95%, although loadings of 80% or less are preferred. The invention also comprises devices which incorporate the nanofiller (e.g., electrical, magnetic, optical, biomedical, and electrochemical devices).

"coating" (a.k.a. "film", "laminate", or "layer") means any deposition comprising submicron and nanoscale powders. The term includes in its scope a substrate, surface, deposition, or a combination thereof having a hollow, dense, porous, semi-porous, coated, uncoated, simple, complex, dendritic, inorganic, organic, composite, doped, undoped, uniform, non-uniform, surface functionalized, surface non-functionalized, thin, thick, pretreated, post-treated, stoichiometric, or non-stoichiometric form or morphology.

"agglomerated" means a powder in which at least some individual particles of the powder adhere to neighboring particles, primarily by electrostatic forces.

"aggregated" means a powder in which at least some individual particles are chemically bonded to neighboring particles.

"supramolecular electronics" means the assemblies of pi-conjugated systems on the 5 to 100 nanometer length scale that are prepared by self-assembly with the aim to fit these structures between electrodes.

"atomic force microscope ("AFM")" means a very high-resolution type of scanning probe microscope, with demonstrated resolution of fractions of an Angstrom, more than 1000 times better than the optical diffraction limit. The AFM is one of the foremost tools for imaging, measuring and manipulating matter at the nanoscale.

"scanning tunneling microscope ("STM")" means a non-optical microscope that scans an electrical probe over a surface to be imaged to detect a weak electric current flowing between the tip and the surface. The STM allows visualize regions of high electron density and hence infer the position of individual atoms and molecules on the surface of a lattice. The STM is capable of higher resolution than the atomic force microscope (AFM)

"biosensor" means a device for the detection of an analyte that combines a biological component with a physicochemical detector component. A biosensor comprises three parts: (i) a sensitive biological element (i.e. biological material, including but not limited to, tissue, microorganisms, organelles, cell receptors, enzymes, antibodies, nucleic acids, amino acids, etc) or a biologically derived material or biomimic; (ii) a transducer; (iii) a detector element (i.e. chemical, physiochemical, optical, piezoelectric, electrochemical; thermometric, or magnetic).

"optical biosensor" means a biosensor that utilizes the behavior and properties of light and the interaction of light with matter as the detector element.

"optical switch" means a switch that enables signals in optical fibers or integrated optical circuits (IOCs) to be selectively switched from one circuit to another.

"interface" means the communication boundary between two or more entities, such as a piece of software, a hardware device, or a user. It generally refers to an abstraction that an entity provides of itself to the outside. This separates the methods of external communication from internal operation, and allows it to be internally modified without affecting the way outside entities interact with it, as well as provide multiple abstractions of itself. It may also provide a means of translation between entities which do not speak the same language, such as between a human and a computer. The interface between a human and a computer is called a user interface. Interfaces between hardware components are physical interfaces. Interfaces between software exist between separate software components and provide a programmatic mechanism by which these components can communicate.

"pi-conjugated systems" (a.k.a. "stacking") means the noncovalent interaction between organic compounds containing aromatic moieties. $\pi$-$\pi$ interactions are caused by intermolecular overlapping of p-orbitals in $\pi$-conjugated systems, so they become stronger as the number of $\pi$-electrons increases.

"quantum dots" means a semiconductor nanostructure that confines the motion of conduction band electrons, valence band holes, or excitons (pairs of conduction band electrons and valence band holes) in all three spatial directions. The confinement can be due to electrostatic potentials (generated by external electrodes, doping, strain, impurities), due to the presence of an interface between different semiconductor materials (e.g. in the case of self-assembled quantum dots), due to the presence of the semiconductor surface (e.g. in the case of a semiconductor nanocrystal), or due to a combination of these. A quantum dot has a discrete quantized energy spectrum.

"molecular self-assembly" means the assembly of molecules without guidance or management from an outside source.

"nanocomposite" means materials that are created by introducing nanoparticulates into a macroscopic sample material. The nanomaterials add to the electrical and thermal conductivity as well as to the mechanical strength properties of the original material. In general, the nanomaterial used are carbon nanotubes and they are dispersed into the other composite materials during processing. The percentage by weight of the nanomaterials introduced is able to remain very low (on the order of 0.5%-5%) due to the incredibly high surface area to volume ratio of the particles.

"molecular electronics" (a.k.a. moletronics) means an interdisciplinary themed materials science in which the unifying feature is the use of molecular building blocks for the fabrication of electronic components, both passive (e.g. resistive wires) and active (e.g transistors). Molecular electronics provides a means to extend Moore's Law beyond the foreseen limits of small-scale conventional silicon integrated circuits.

"Moore's law" means the empirical observation made in 1965 that the number of transistors on an integrated circuit for minimum component cost doubles every 24 months. It is attributed to Gordon E. Moore (born 1929), a co-founder of Intel.

"supramolecular chemistry" means the area of chemistry which focuses on the noncovalent bonding interactions of molecules. Traditional organic synthesis involves the making and breaking of covalent bonds to construct a desired molecule.

"molecular recognition" means a chemical event in which a host molecule is able to form a complex with a second molecule (i.e. the guest). This process occurs through non-covalent chemical bonds, including but not limited to, hydrogen bonding, hydrophobic interactions, ionic interaction.

"static molecular recognition" means a 1:1 type complexation reaction between a host molecule and a guest molecule (an analogy is the interaction between a key and a keyhole.) To achieve advanced static molecular recognition, it is necessary to make recognition sites that are specific for guest molecules.

"dynamic molecular recognition" means a reaction that dynamically changes the equilibrium to an n:m type host-guest complex by a recognition guest molecule. Dynamic molecular recognition appearing in supermolecules is essential for designing highly functional chemical sensors and molecular devices.

"rotaxane" means a mechanically-interlocked molecular architecture consisting of a dumbbell-shaped molecule that is threaded through a macrocycle or ring-like molecule. The two components are kinetically trapped as the two end-groups of the dumbbell (often called stoppers) are larger than the internal diameter of the ring, and thus prevent dissociation (unthreading) since this would require significant distortion of the covalent bonds. The name, rotaxane, is derived from the Latin for wheel (rota) and axle (axis).

"synthetic molecular motors" means nanoscale devices capable of rotation under energy input. The basic requirements for a synthetic motor are repetitive 360° motion, the consumption of energy, and unidirectional rotation. Examples include but are not limited to triptycence motors and helicene.

"abstraction" means the separation of the logical properties of data or function from its implementation in a computer program.

"access time" means the time interval between the instant at which a call for data is initiated and the instant at which the delivery of the data is completed.

"adaptive maintenance" means software maintenance performed to make a computer program usable in a changed environment.

"algorithm" means any sequence of operations for performing a specific task.

"algorithm analysis" means a software verification and validation ("V&V") task to ensure that the algorithms selected are correct, appropriate, and stable, and meet all accuracy, timing, and sizing requirements.

"analog" means pertaining to data [signals] in the form of continuously variable [wave form] physical quantities; e.g., pressure, resistance, rotation, temperature, voltage.

"analog device" means a device that operates with variables represented by continuously measured quantities such as pressures, resistances, rotations, temperatures, and voltages.

"analog-to-digital converter" means input related devices which translate an input device's [sensor] analog signals to the corresponding digital signals needed by the computer.

"analysis" means a course of reasoning showing that a certain result is a consequence of assumed premises.

"application software" means software designed to fill specific needs of a user.

"bar code" means a code representing characters by sets of parallel bars of varying thickness and separation that are read optically by transverse scanning.

"basic input/output system" means firmware that activates peripheral devices in a PC. Includes routines for the keyboard, screen, disk, parallel port and serial port, and for internal services such as time and date. It accepts requests from the device drivers in the operating system as well from application programs. It also contains autostart functions that test the system on startup and prepare the computer for operation. It loads the operating system and passes control to it.

"batch processing" means execution of programs serially with no interactive processing.

"benchmark" means a standard against which measurements or comparisons can be made.

"block" means a string of records, words, or characters that for technical or logical purposes are treated as a unity.

"block check" means the part of the error control procedure that is used for determining that a block of data is structured according to given rules.

"block diagram" means a diagram of a system, instrument or computer, in which the principal parts are represented by suitably annotated geometrical figures to show both the basic functions of the parts and the functional relationships between them.

"blueprint" means an detailed plan or outline.

"boot" means to initialize a computer system by clearing memory and reloading the operating system. A distinction can be made between a warm boot and a cold boot. A cold boot means starting the system from a powered-down state. A warm boot means restarting the computer while it is powered-up. Important differences between the two procedures are; 1) a power-up self-test, in which various portions of the hardware [such as memory] are tested for proper operation, is performed during a cold boot while a warm boot does not normally perform such self-tests, and 2) a warm boot does not clear all memory.

"bootstrap" means a short computer program that is permanently resident or easily loaded into a computer and whose execution brings a larger program, such an operating system or its loader, into memory.

"boundary value" means a data value that corresponds to a minimum or maximum input, internal, or output value specified for a system or component.

"boundary value analysis" means a selection technique in which test data are chosen to lie along "boundaries" of the input domain [or output range] classes, data structures, procedure parameters, etc.

"branch analysis" means a test case identification technique which produces enough test cases such that each decision has a true and a false outcome at least once.

"calibration" means ensuring continuous adequate performance of sensing, measurement, and actuating equipment with regard to specified accuracy and precision requirements.

"certification" means technical evaluation, made as part of and in support of the accreditation process that establishes the extent to which a particular computer system or network design and implementation meet a pre-specified set of requirements.

"change control" means the processes, authorities for, and procedures to be used for all changes that are made to the computerized system and/or the system's data. Change control is a vital subset of the Quality Assurance [QA] program within an establishment and should be clearly described in the establishment's SOPs.

"check summation" means a technique for error detection to ensure that data or program files have been accurately copied or transferred.

"compiler" means computer program that translates programs expressed in a high-level language into their machine language equivalents.

"computer system audit" means an examination of the procedures used in a computer system to evaluate their effectiveness and correctness and to recommend improvements.

"computer system security" means the protection of computer hardware and software from accidental or malicious access, use, modification, destruction, or disclosure.

"concept phase" means the initial phase of a software development project, in which user needs are described and evaluated through documentation.

"configurable, off-the-shelf software" means application software, sometimes general purpose, written for a variety of industries or users in a manner that permits users to modify the program to meet their individual needs.

"control flow analysis" means a software V&V task to ensure that the proposed control flow is free of problems, such as design or code elements that are unreachable or incorrect.

"controller" means hardware that controls peripheral devices such as a disk or display screen. It performs the physical data transfers between main memory and the peripheral device.

"conversational" means pertaining to a interactive system or mode of operation in which the interaction between the user and the system resembles a human dialog.

"coroutine" means a routine that begins execution at the point at which operation was last suspended, and that is not required to return control to the program or subprogram that called it.

"corrective maintenance" means maintenance performed to correct faults in hardware or software.

"critical control point" means a function or an area in a manufacturing process or procedure, the failure of which, or loss of control over, may have an adverse affect on the quality of the finished product and may result in an unacceptable health risk.

"data analysis" means evaluation of the description and intended use of each data item in the software design to ensure the structure and intended use will not result in a hazard. Data structures are assessed for data dependencies that circumvent isolation, partitioning, data aliasing, and fault containment issues affecting safety, and the control or mitigation of hazards.

"data integrity" means the degree to which a collection of data is complete, consistent, and accurate.

"data validation" means a process used to determine if data are inaccurate, incomplete, or unreasonable. The process may include format checks, completeness checks, check key tests, reasonableness checks and limit checks.

"design level" means the design decomposition of the software item; e.g., system, subsystem, program or module.

"design phase" means the period of time in the software life cycle during which the designs for architecture, software components, interfaces, and data are created, documented, and verified to satisfy requirements.

"diagnostic" means pertaining to the detection and isolation of faults or failures.

"different software system analysis" means Analysis of the allocation of software requirements to separate computer systems to reduce integration and interface errors related to safety. Performed when more than one software system is being integrated.

"dynamic analysis" means analysis that is performed by executing the program code.

"encapsulation" means a software development technique that consists of isolating a system function or a set of data and the operations on those data within a module and providing precise specifications for the module.

"end user" means a person, device, program, or computer system that uses an information system for the purpose of data processing in information exchange.

"error detection" means techniques used to identify errors in data transfers.

"error guessing" means the selection criterion is to pick values that seem likely to cause errors.

"error seeding" means the process of intentionally adding known faults to those already in a computer program for the purpose of monitoring the rate of detection and removal, and estimating the number of faults remaining in the program.

"failure analysis" means determining the exact nature and location of a program error in order to fix the error, to identify and fix other similar errors, and to initiate corrective action to prevent future occurrences of this type of error.

"Failure Modes and Effects Analysis" means a method of reliability analysis intended to identify failures, at the basic component level, which have significant consequences affecting the system performance in the application considered.

"FORTRAN" means an acronym for FORmula TRANslator, the first widely used high-level programming language. Intended primarily for use in solving technical problems in mathematics, engineering, and science.

"life cycle methodology" means the use of any one of several structured methods to plan, design, implement, test and operate a system from its conception to the termination of its use.

"logic analysis" means evaluates the safety-critical equations, algorithms, and control logic of the software design.

"low-level language" means the advantage of assembly language is that it provides bit-level control of the processor allowing tuning of the program for optimal speed and performance. For time critical operations, assembly language may be necessary in order to generate code which executes fast enough for the required operations.

"maintenance" means activities such as adjusting, cleaning, modifying, overhauling equipment to assure performance in accordance with requirements.

"modulate" means varying the characteristics of a wave in accordance with another wave or signal, usually to make user equipment signals compatible with communication facilities.

"Pascal" means a high-level programming language designed to encourage structured programming practices.

"path analysis" means analysis of a computer program to identify all possible paths through the program, to detect incomplete paths, or to discover portions of the program that are not on any path.

"quality assurance" means the planned systematic activities necessary to ensure that a component, module, or system conforms to established technical requirements.

"quality control" means the operational techniques and procedures used to achieve quality requirements.

"software engineering" means the application of a systematic, disciplined, quantifiable approach to the development, operation, and maintenance of software.

"software engineering environment" means the hardware, software, and firmware used to perform a software engineering effort.

"software hazard analysis" means the identification of safety-critical software, the classification and estimation of potential hazards, and identification of program path analysis to identify hazardous combinations of internal and environmental program conditions.

"software reliability" means the probability that software will not cause the failure of a system for a specified time under specified conditions.

"software review" means an evaluation of software elements to ascertain discrepancies from planned results and to recommend improvement.

"software safety change analysis" means analysis of the safety-critical design elements affected directly or indirectly by the change to show the change does not create a new hazard, does not impact on a previously resolved hazard, does not make a currently existing hazard more severe, and does not adversely affect any safety-critical software design element.

"software safety code analysis" means verification that the safety-critical portions of the design are correctly implemented in the code.

"software safety design analysis" means verification that the safety-critical portion of the software design correctly implements the safety-critical requirements and introduces no new hazards.

"software safety requirements analysis" means analysis evaluating software and interface requirements to identify errors and deficiencies that could contribute to a hazard.

"software safety test analysis" means analysis demonstrating that safety requirements have been correctly implemented and that the software functions safely within its specified environment.

"system administrator" means the person that is charged with the overall administration, and operation of a computer system. The System Administrator is normally an employee or a member of the establishment.

"system analysis" means a systematic investigation of a real or planned system to determine the functions of the system and how they relate to each other and to any other system.

"system design" means a process of defining the hardware and software architecture, components, modules, interfaces, and data for a system to satisfy specified requirements.

"top-down design" means pertaining to design methodology that starts with the highest level of abstraction and proceeds through progressively lower levels.

"traceability analysis" means the tracing of Software Requirements Specifications requirements to system requirements in concept documentation.

"validation" means establishing documented evidence which provides a high degree of assurance that a specific process will consistently produce a product meeting its predetermined specifications and quality attributes.

"validation, process" means establishing documented evidence which provides a high degree of assurance that a specific process will consistently produce a product meeting its predetermined specifications and quality characteristics.

"validation, prospective" means validation conducted prior to the distribution of either a new product, or product made under a revised manufacturing process, where the revisions may affect the product's characteristics.

"validation protocol" means a written plan stating how validation will be conducted, including test parameters, product characteristics, production equipment, and decision points on what constitutes acceptable test results.

"validation, retrospective" means validation of a process for a product already in distribution based upon accumulated production, testing and control data. Retrospective validation can also be useful to augment initial premarket prospective validation for new products or changed processes. Test data is useful only if the methods and results are adequately specific. Whenever test data are used to demonstrate conformance to specifications, it is important that the test methodology be qualified to assure that the test results are objective and accurate.

"validation, software" means. determination of the correctness of the final program or software produced from a development project with respect to the user needs and requirements. Validation is usually accomplished by verifying each stage of the software development life cycle.

"structured query language" means a language used to interrogate and process data in a relational database. Originally developed for IBM mainframes, there have been many implementations created for mini and micro computer database applications. SQL commands can be used to interactively work with a data base or can be embedded with a programming language to interface with a database.

"Batch" means a specific quantity of a drug or other material that is intended to have uniform character and quality, within specified limits, and is produced according to a single manufacturing order during the same cycle of manufacture.

"Component" means any ingredient intended for use in the manufacture of a drug product, including those that may not appear in such drug product.

"Drug product" means a finished dosage form, for example, tablet, capsule, solution, etc., that contains an active drug ingredient generally, but not necessarily, in association with inactive ingredients. The term also includes a finished dosage form that does not contain an active ingredient but is intended to be used as a placebo.

"Active ingredient" means any component that is intended to furnish pharmacological activity or other direct effect in the diagnosis, cure, mitigation, treatment, or prevention of disease, or to affect the structure or any function of the body of man or other animals. The term includes those components that may undergo chemical change in the manufacture of the drug product and be present in the drug product in a modified form intended to furnish the specified activity or effect.

"Inactive ingredient" means any component other than an active ingredient.

"in-process material" means any material fabricated, compounded, blended, or derived by chemical reaction that is produced for, and used in, the preparation of the drug product.

"Lot number, control number, or batch number" means any distinctive combination of letters, numbers, or symbols, or any combination thereof, from which the complete history of the manufacture, processing, packing, holding, and distribution of a batch or lot of drug product or other material can be determined.

"Quality control unit" means any person or organizational element designated by the firm to be responsible for the duties relating to quality control.

"Acceptance criteria" means the product specifications and acceptance/rejection criteria, such as acceptable quality level and unacceptable quality level, with an associated sampling plan, that are necessary for making a decision to accept or reject a lot or batch.

"Manufacturing execution system" (a.k.a. MES) means an integrated hardware and software solution designed to measure and control activities in the production areas of manufacturing organizations to increase productivity and improve quality.

"Process analytical technology" (a.k.a. PAT) means a mechanism to design, analyze, and control pharmaceutical manufacturing processes through the measurement of critical process parameters and quality attributes.

"New molecular entity" (a.k.a. NME or New Chemical Entity ("CNE")) means a drug that contains no active moiety that has been approved by FDA. An active moiety means the molecule or ion, excluding those appended portions of the molecule that cause the drug to be an ester, salt (including a salt with hydrogen or coordination bonds), or other noncovalent derivative (such as a complex, chelate, or clathrate) of the molecule, responsible for the physiological or pharmacological action of the drug substance.

"Crystallization process" means the natural or artificial process of formation of solid crystals from a homogeneous solution consisting of two (2) major steps, (i) nucleazation and (ii) crystal growth.

"Tablet press" means the apparatus or machine which compresses powder into a tablet by the action of one upper and one lower punch sliding along closing cam tracks and meeting together at a predetermined point in a die between the two main pressure rolls.

"Chromatography" means collectively a family of laboratory techniques for the separation of mixtures. It involves passing a mixture which contains the analyte through a stationary phase, which separates it from other molecules in the mixture and allows it to be isolated.

"pH" means is a measure of the activity of hydrogen ions ($H^+$) in a solution and, therefore, its acidity.

II.) NANOMATERIAL

The present invention provides for nanomaterials which are manufactured to achieve a desired function or property that will assist in the manufacturing of drugs. Nanomaterials of the inventions comprise nanostructures, nanocrystals, nanowires, nanotubes, nanofillers, nanocomposites, and precursors or any combination thereof. The nanomaterials useful in the present invention can also further comprise ligands conjugated, cooperated, associated or attached to their surface as described throughout. Suitable ligands include any group known to those skilled in the art. Use of such ligands can enhance the ability of the nanocrystals to incorporate into various solvents and matrixes, including polymers. Increasing the miscibility (i.e., the ability to be mixed without separation) of the nanocrystals in various solvents and matrixes allows them to be distributed throughout a polymeric composition such that the nanocrystals do not aggregate together and therefore do not scatter light. Such ligands are described as "miscibility-enhancing" ligands herein.

In a further embodiment, the invention provides polymeric layers comprising a polymer and nanocrystals embedded within the polymer, such that the layers act as photon-filtering nanocomposites. Suitably, the nanocrystals will be prepared from semiconductor materials, but any suitable material described throughout can be used to prepare the nanocrystals. In certain embodiments, the nanocrystals will have a size and a composition such that the nanocrystals absorb light of a particular wavelength or over a range of wavelengths. As such, the nanocrystals utilized in these embodiments are tailored such that their absorption characteristics are enhanced or maximized, while their emission characteristics are minimized, i.e. they will absorb light in a highly efficient manner, but suitably will emit only a very low level, or preferably no light. In other embodiments, however, the photon-filtering nanocomposites can also comprise nanocrystals that have high emission properties and emit light at a particular wavelength as discussed throughout. As such, the present invention provides nanocomposites that comprise different types of nanocrystals such that the nanocomposites exhibit several, or all, of the properties discussed throughout, in a layer. In embodiments of the present invention where the photon-filtering polymeric layers are used to coat optical devices, such optical devices can be refractive (e.g., lenses) or reflective (e.g., mirrors).

Additionally, in certain embodiments of the present invention where the photon-filtering polymeric layers are used to encapsulate active devices, such active devices can be any device known to the skilled artisan. As used herein an "active device" is one that requires a source of energy for its operation and has an output that is a function of present and past input signals. Examples of active devices include, but are not limited to, controlled power supplies, transistors, diodes, including light emitting diodes (LEDs), light detectors, amplifiers, transmitters and other semiconductor devices in basic input/output systems ("I/O").

By controlling the size and composition of the nanocrystals used in the practice of the present invention, the nanocrystals will absorb light of a particular wavelength, or a particular range of wavelengths, while not scattering light. The ability to make nanocrystals out of different semiconductors, and control their size, allows for polymeric layers to be fabricated with nanocrystals that will absorb light from the UV, to visible, to near infrared (NIR), to infrared (IR) wavelengths. Nanocrystals for use in the present invention will suitably be less than about 100 nm in size, and down to less than about 2 nm in size. In suitable embodiments, the nanocrystals of the present invention absorb visible light. As used herein, visible light is electromagnetic radiation with wavelengths between about 380 and about 780 nanometers that is visible to the human eye. Visible light can be separated into the various colors of the spectrum, such as red, orange, yellow, green, blue, indigo and violet. The photon-filtering nanocomposites of the present invention can be constructed so as to absorb light that makes up any one or more of these colors. For example, the nanocomposites of the present invention can be constructed so as to absorb blue light, red light, or green light, combinations of such colors, or any colors in between. As used herein, blue light comprises light between about 435 nm and about 500 nm, green light comprises light between about 520 nm and 565 nm and red light comprises light between about 625 nm and about 740 nm in wavelength. One of ordinary skill will be able to construct nanocomposites that can filter any combination of these wavelengths, or wavelengths between these colors, and such nanocomposites are embodied by the present invention.

As disclosed herein, the nanocrystals useful in the practice of the present invention can have a composition and a size such that they absorb light at a particular wavelength(s) and emit at a particular wavelength(s). In certain embodiments, the polymeric layers of the present invention can comprise combinations of nanocrystals that function in the various ways described herein. For example, a nanocomposite of the present invention can comprise nanocrystals having specific, enhanced emission properties, others having specific, enhanced absorption properties but low emission properties, and the entire nanocomposite can be constructed such that the layer has a specific refractive index that is matched or tailored for a specific purpose. Combined in such a way, the polymeric layers of the present invention can be used as encapsulates for active devices (e.g., LEDs) that emit light of a certain wavelength, filter out other wavelengths and have a refractive index appropriately matched to an active device and/or an additional substrate or coating.

In preferred embodiments, it is desirable that the nanocrystals do not aggregate. That is, that they remain separate from each other in the polymeric layer and do not coalesce with one another to form larger aggregates. This is important, as individual crystals will not scatter light passing through the layer, while larger aggregated structures can create an opaque layer that can hinder the passage of light. However, depending on the parameters of the pharmaceutical manufacturing process in which the nanomaterials are used the degree of aggregation may need to be modified to achieve the desired result.

Dispersion of nanocrystals in a host matrix can be controlled by minimizing phase separation and aggregation that can occur when mixing the nanocrystals into the matrixes. A basic strategies known in the art is to design a 3-part ligand, in which the head-group, tail-group and middle/body-group can each be independently fabricated and optimized for their particular function, and then combined into an ideally functioning complete surface ligand. In on embodiment, the head group is selected to bind specifically to the semiconductor material of the nanocrystal. In one embodiment, the tail group is designed to interact strongly with the matrix material and be miscible in the solvent utilized (and can, optionally, contain a linker group to the host matrix) to allow maximum miscibility and loading density in the host matrix without nanocrystal aggregation. In one embodiment, the middle or body group is selected for specific electronic functionality (e.g., charge isolation, Input/output, detector, etc).

In another aspect of the invention nanomaterials comprise nanowires. While the example implementations described herein principally use Si, other types of nanowires (and other nanostructures such as nanoribbons, nanotubes, nanorods and the like) can be used including semiconductive nanowires, that are comprised of semiconductor material selected from, e.g., Si, Ge, Sn, Se, Te, B, C (including diamond), P, B—C, B—P(BP6), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN2, CaCN2, ZnGeP2, CdSnAs2, ZnSnSb2, CuGeP3, CuSi2P3, (Cu, Ag)(Al, Ga, In, Tl, Fe)(S, Se, Te)2, Si3N4, Ge3N4, Al.sub.2O.sub.3, (Al, Ga, In)2 (S, Se, Te)3, Al2CO, and an appropriate combination of two or more such semiconductors.

Additionally, the nanowires of the invention can include carbon nanotubes, or conductive or semiconductive organic polymer materials, (e.g., pentacene, and transition metal oxides).

In another aspect of the invention, nanomaterials of the invention comprise nanotubes. Nanotubes can be formed in combinations/thin films of nanotubes as is described herein for nanowires, alone or in combination with nanowires, to provide the properties and advantages described herein.

a. Functional Properties of Nanomaterials

In one aspect of the invention nanomaterials are used in the pharmaceutical manufacturing process. In one embodiment, the nanomaterial is designed to include a functional property. The preferred functional property is one that provides a synergy with the pharmaceutical manufacturing process that the nanomaterial is being utilized. For example, nanomaterials may possess optical properties useful in detection of particulates or contaminates in gas or aerosols. In another example, a nanomaterial may possess thermal properties whereby deviations in temperature may be detected.

A very wide variety of pure phase materials such as polymers are now readily known in the art. However, low cost pure phase materials are somewhat limited in the achievable ranges of a number of properties, including, for example, electrical conductivity, magnetic permeability, dielectric constant, and thermal conductivity. In order to circumvent these limitations, it has become common to form composites, in which a matrix is blended with a filler material with desirable properties.

In one embodiment, the invention comprises a nanofiller, intimately mixed with a matrix to form a nanostructured composite. At least one of the nanostructured filler and the nanostructured composite has a desired material property which differs by at least 20% from the same material property for a micron-scale filler or a micron-scale composite, respectively. The desired material property is selected from the group consisting of refractive index, transparency to light, reflection characteristics, resistivity, permittivity, permeability, coercivity, B-H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility and wear rate.

The nanofiller may comprise one or more elements selected from the s, p, d, and f groups of the periodic table, or it may comprise a compound of one or more such elements with one or more suitable anions, such as aluminum, antimony, boron, bromine, carbon, chlorine, fluorine, germanium, hydrogen, indium, iodine, nickel, nitrogen, oxygen, phosphorus, selenium, silicon, sulfur, or tellurium. The matrix may be a polymer (e.g., poly(methyl methacrylate), poly(vinyl alcohol), polycarbonate, polyalkene, or polyaryl), a ceramic (e.g., zinc oxide, indium-tin oxide, hafnium carbide, or ferrite), or a metal (e.g., copper, tin, zinc, or iron). Loadings of the nanofiller may be as high as 95%, although loadings of 80% or less are preferred. The invention also comprises devices which incorporate the nanofiller (e.g., electrical, magnetic, optical, biomedical, and electrochemical devices).

(i) Nanomaterial with Thermal Conductivity

In one aspect of the invention, the nanomaterial possesses the functional property of thermal conductivity. Any nanoparticle that can be functionalized and which has a higher thermal conductivity than the organic matrix can be used to prepare the present compositions. Suitable nanoparticles include but are not limited to colloidal silica, polyhedral oligomeric silsesquioxane ("POSS"), nano-sized metal oxides (e.g. alumina, titania, zirconia), nano-sized metal nitrides (e.g. boron nitrides, aluminum nitrides) and nano-metal particles (e.g., silver, gold, or copper nanoparticles). In particularly useful embodiments, the nanoparticles are organo-functionalized POSS materials or colloidal silica. Colloidal silica exists as a dispersion of submicron-sized silica ($SiO_2$) particles in an aqueous or other solvent medium. The colloidal silica contains up to about 85 weight % of silicon dioxide ($SiO_2$) and typically up to about 80 weight % of silicon dioxide. The particle size of the colloidal silica is typically in a range between about 1 nanometers ("nm") and about 250 nm, and more typically in a range between about 5 nm and about 150 nm. The fillers used are micron-sized thermally conductive materials and can be reinforcing or non-reinforcing. In one embodiment, the present nanomaterial with thermal functionality can be formed into sheets and cut into any desired shape. In a preferred embodiment, the nanomaterials can advantageously be used for thermal interface pads and positioned on thermal biosensors.

(ii) Nanomaterial with Porosity/Permeability

In one embodiment, nanomaterials possess predefined porosity and permeability properties. The properties are useful in the design of filters that are used in the pharmaceutical manufacturing process. The filers can be used for such process as purification, etc. The nanomaterials are designed with a membrane or layer is designed to block certain objects or substances while letting others through. The porosity/permeability properties of the nanomaterials can be used to separate liquids from liquids, solids from liquids, gas from liquids, or any combination of thereof. In a preferred embodiment, the porosity/permeability properties are designed to be advantageous to the manufacturing of pharmaceuticals.

(iii) Nanomaterial with Enhanced Luminescence

In one embodiment, nanomaterials possess enhanced luminescent properties. The nanomaterials are made from nanopowders using standard methods known in the art. For example, luminescent nanomaterial is prepared using the following steps: forming a homogenized precursor solution of at least one lanthanide group metal precursor and at least one lanthanide series dopant precursor; adding a phosphate source and a fuel to the precursor solution; removing water from the precursor solution to leave a reaction concentrate; and igniting the reaction concentrate to form a powder comprising the plurality of nanoparticles. The nanomaterials of the invention can be used in pharmaceutical manufacturing applications such as, display devices, fluorescent lamps, compact fluorescent lamps, linear fluorescent lamps, light emitting diodes, and imaging applications. In a preferred embodiment, the nanomaterials will be used in the quality control imaging of pharmaceuticals.

(iv) Nanomaterial with Enhanced Acoustics

In one embodiment, nanomaterials possess enhanced acoustic functions. The nanomaterials are made from using standard methods known in the art. For example, a surface acoustic wave device fabricated on a lithium niobate substrate and a sensing bilayer positioned on the acoustic path of the surface acoustic wave device, the sensing bilayer further comprising nanocrystalline or other nanomaterial such as nanoparticles or nanowires of palladium and metal free phthalocyanine. Preferably, the surface acoustic wave device has a center frequency of about 200 MHz. Nanomaterials with enhanced acoustic properties will respond to gases (i.e. hydrogen, helium, etc.) in near real time, at low (room) temperature, without being affected by $CO_2$, $CH_4$ and other gases, in air ambient or controlled ambient, providing sensitivity to low ppm levels. In a preferred embodiment, the nanomaterials will detect gases used in the manufacturing of pharmaceuticals.

(v) Nanomaterial with Enhanced Magnetic Properties

In one embodiment, nanomaterials possess enhanced magnetic functions. The nanomaterials are made from using standards known in the art. For example, a solvent, preferably an ether or an aromatic solvent such as toluene, anisole, dioctylether, or the like, is added to a carboxylic acid, preferably Oleic acid, or the like. An amine, preferably Oleylamine or the like is then added to the solvent and Oleic acid solution to complete solution A. It will be appreciated that other solvents or amines not listed here may be used to perform the same decomposition. The solution A is added to a metal-organic precursor to form solution B. Solution B is then heated, for example by radiation at approximately 150 degrees C. in anisole for approximately 48 hours, under pressure, for example 3 Bars of H2. Nanorods begin to appear. The nanorods are crystalline hexagonal close packed (hcp), and grow along the c axis of the structure. The nanorods are in a thermodynamically stable form of cobalt after completion of the reaction. These thermodynamically stable cobalt nanorods will not rearrange into other forms such as spherical nanoparticles or any other form.

The nanoparticles that result from this embodiment exhibit magnetic properties, such as for example: i) saturation magnetization similar to the magnetic characteristics and properties of bulk cobalt; ii) enhanced magnetic anisotropy and strongly enhanced coercive magnetic field (as compared to bulk cobalt and spherical nanoparticles) due to the shape anisotropy. The nanomaterials with enhanced magnetic properties will allow particle orientation in magnetic fields to optimize high-frequency device applications. In a preferred embodiment, the high-frequency device will be used in the pharmaceutical manufacturing process.

(vi) Nanomaterial with Enhanced Solubility

In one embodiment, nanomaterials possess enhanced solubility properties. The nanomaterials are made from using standards known in the art. For example, a rigid poly(aryleneethynylene) polymer is coupled with a para-diethynyl-($R_1$-$R_x$)arylene and an ($R_1$-$R_y$)-para-dih-aloarylene in the presence of a first polymerization-terminating haloaryl agent under conditions and for a period of time to produce fluorescence. Then terminating the coupling by addition of a second polymerization-terminating haloaryl agent, the second haloaryl agent having equal or greater activity for coupling as compared to the ($R_1$-$R_y$)-para-dihaloarylene. The nanomaterials with enhanced solubility will provide for functional nanomaterials that can be used for epoxy and engineering plastic composites, filters, actuators, adhesive composites, elastomer composites, materials for thermal management (interface materials, materials for heat transfer applications), improved dimensionally stable structures for sensorsoptoelectronic or microelectromechanical components or subsystems, rapid prototyping materials, composite fibers, etc. In a preferred embodiment, the nanomaterial will be used in the pharmaceutical manufacturing process.

(vii) Shape Engineered Nanomaterials

In one embodiment, nanomaterials are engineered for specific shapes or mechanical properties. The nanomaterials are made from using standards known in the art. For example, nanomaterials are made with modified degree of agglomeration. Additionally, nanomaterials are made with a modified surface area. Additionally, nanomaterials are made with post-processing to modify the phase and shape. Additionally, post-processing is utilized to achieve consolidation. Nanomaterials that are shape engineered are used for ceramic, metal, or composite seals. Additionally as filters with a defined porosity gradient, monitors, sensors, drug delivery devices, and biocatalysts from nanoscale powders using the multi-layer laminating process to produce three-dimensional shapes. In a preferred embodiment, the nanomaterials will be used in pharmaceutical manufacturing.

(viii) Nanomaterials Will Enhanced Optical Properties

In one embodiment, nanomaterials are engineered with enhanced optical properties. The nanomaterials are made from using standards known in the art. Generally, in optical lenses, the optical path length varies with distance from its center, where optical path length is defined as the product of the physical path length, thickness, and the refractive index, n, of the lens material. In the most common lenses, the refractive index, n, is fixed and the thickness, varies. However, a lens can also be created by keeping the thickness, constant and varying the refractive index as a function of distance from the axis of the lens. Such a lens is called a Graded Index lens, or sometimes abbreviated as a GRIN lens. The methods of the present invention can also be used to create GRIN lenses. Polymer/nanocrystal blends can be used to make GRIN lenses due to the dramatic refractive index difference between nanocrystals (e.g., ZnS about 2.35) and optical plastics such as poly(methyl methacrylate) (PMMA) (refractive index about 1.45). With normal glass, a difference of about 0.05 refractive index units is achievable over about 8 mm. Utilizing the methods and processes of the present application, a difference of about 0.20 refractive index units over about 8 mm can be achieved to make much more powerful lenses. Nanomaterials with enhanced optical properties can be used for contact sensors, remote sensors, LIDAR, optical parametric oscillators, optical data storage, optical spectroscopy, optical amplifiers, wavelength translation devices, super sensitive optical detection, and optical switches. In a preferred embodiment, the sensors with enhanced optical properties are used to monitor and manufacture pharmaceuticals.

III.) SENSORS

In one embodiment, the invention relates to sensors that are used in the monitoring and manufacturing of pharmaceuticals. In a preferred embodiment, the sensors are made from nanomaterials disclosed herein and are developed on a microscopic scale using MEMS (micro-electrical-mechanical-systems) technology. In one embodiment, the sensor is made from $1^{st}$ generation MEMS technology (i.e. a sensor element mostly based on a silicon or similar structure, sometimes combined with analog amplification on a nanomaterial). In one embodiment, the sensor is made from $2^{nd}$ generation MEMS technology (i.e. a sensor element combined with analog amplification and analog-to-digital converter on one nanomaterial). In a preferred embodiment, the sensor is made from $3^{rd}$ generation MEMS technology (i.e. fusion of the sensor element with analog amplification, analog-to-digital converter and digital intelligence for linearization and temperature compensation on the same nanomaterial). In another preferred embodiment, the sensor is made from $4^{th}$ generation MEMS technology (i.e. memory cells for calibration and temperature compensation data are added to the elements of the $3^{rd}$ generation sensor). The advantages of using sensors made out of nanomaterials is the sensors can reach significantly higher speeds and sensitivity that macroscale sensors.

It will be appreciated by one of skill in the art that the type of sensor needed will be a direct function to the pharmaceutical manufacturing process that is being monitored and for what purpose. For example, monitoring the levels of contaminate in an active ingredient will require different monitoring parameters that monitoring the temperature of pH of a final product. In these situations, it will be appreciated by one of ordinary skill that either (i) the same sensors can be used with different detecting criteria or (ii) different types of sensors can be used to achieve the best level of monitoring.

Accordingly, sensors of the present invention comprise thermal, electromagnetic, mechanical, chemical, optical, radiation, acoustic, and biological sensors. In one embodiment, thermal sensors include but are not limbed to thermometers, thermocouples, temperature sensitive resistors, bolometers, calorimeter.

In a further embodiment, electromagnetic sensors include but are not limited to ohmmeters, multimeters, galvanometers, ammeters, leaf electroscopes, watt-hour meters, magnetic compasses, fluxgate compasses, magnetometers, and metal detectors.

In a further embodiment, mechanical sensors include but are not limited to barometers, barographs, pressure gauges, air speed indicators, rate of change sensors, flow sensors, anemometers, flow meters, gas meters, water meters, mass flow sensors, acceleration sensors, whisker sensors, Quadrature wheels, and positions switches.

In a further embodiment, chemical sensors include but are not limited to oxygen sensors (a.k.a. $\lambda$ sensors), ion-selective electrodes, pH glass electrodes, and redox electrodes.

In a further embodiment, optical and radiation sensors include but are not limited to RADAR, LIDAR, dosimeters, particle detectors, scintillators, wire chambers, cloud chambers, bubble chambers, infrared sensors, photocells, photodiodes, phototransistors, image sensors; vacuum tube devices, and proximity sensors.

In a further embodiment, acoustic sensors include but are not limited to ultrasounds and SONAR.

In a further embodiment, biological sensors include but are not limited to biosensors that can detect physical aspects of the external environment such as light, motion, temperature, magnetic fields, gravity, humidity, vibration, pressure, electrical fields, and sound. Additionally, biosensors that can detect environmental molecules such as toxins, nutrients, and pheromones are within the scope of the invention. Additionally, biosensors that can detect metabolic parameters such as glucose level and oxygen level are within the scope of the invention.

In another aspect, this invention also includes a method of producing an improved sensor device. A non-stoichiometric nanopowder is sonicated in a solvent to form a slurry. The slurry is brushed onto screen-printed electrodes and allowed to dry at to remove the solvent. A dissolved polymer may also be included in the slurry. The screen-printed electrodes may be gold electrodes on an alumina substrate. The screen may be made from stainless steel mesh at least 8.times.10 inches in size, with a mesh count of 400, a wire diameter of 0.0007 inches, a bias of 45.degree., and a polymeric emulsion of 0.0002 inches.

In another aspect, this invention includes an improved sensor device prepared from a screen printable paste. A nanopowder and polymer are mechanically mixed; a screen-printing vehicle is added to the mixture and further mechanically mixed. The mixture is milled and screen-printed onto prepared electrodes. The paste is allowed to level and dry. This invention also includes the improved sensor devices produced by the above processes.

In another aspect of the invention, thermal sensors are prepared from nanostructured powders. These thermal sensors can be used to monitor aspects of the pharmaceutical manufacturing process including but not limited to monitor radiation, power, heat and mass flow, charge and momentum flow, and phase transformation.

IV.) SOFTWARE PROGRAM AND COMPUTER PRODUCT

The invention provides for a software program that is programmed in a high-level or low-level programming language, preferably a relational language such as structured query language which allows the program to interface with an already existing program or a database. Other programming languages include but are not limited to C, C++, FORTRAN, Java, Perl, Python, Smalltalk and MS visual basic. Preferably, however, the program will be initiated in parallel with the manufacturing process or quality assurance ("QA") protocol. This will allow the ability to monitor the manufacturing and QA process from its inception. However, in some instances the program can be bootstrapped into an already existing program that will allow monitoring from the time of execution (i.e. bootstrapped to configurable off-the-shelf software).

It will be readily apparent to one of skill in the art that the preferred embodiment will be a software program that can be easily modified to conform to numerous software-engineering environments. One of ordinary skill in the art will understand and will be enabled to utilize the advantages of the invention by designing the system with top-down design. The level of abstraction necessary to achieve the desired result will be a direct function of the level of complexity of the process that is being monitored. For example, the critical control point for monitoring an active ingredient versus an inactive ingredient may not be equivalent. Similarly, the critical control point for monitoring an in-process material may vary from component to component and often from batch to batch.

One of ordinary skill will appreciate that to maximize results the ability to amend the algorithm needed to conform to the validation and QA standards set forth by the quality control unit on each step during manufacture will be preferred. This differential approach to programming will provide the greatest level of data analysis leading to the highest standard of data integrity.

The preferred embodiments may be implemented as a method, system, or program using standard software programming and/or engineering techniques to produce software, firmware, hardware, or any combination thereof. The term "computer product" as used herein is intended to encompass one or more computer programs and data files accessible from one or more computer-readable devices, firmware, programmable logic, memory devices (e.g. EEPROM's, ROM's, PROM's, RAM's, SRAM's, etc.) hardware, electronic devices, a readable storage diskette, CD-ROM, a file server providing access to programs via a network transmission line, wireless transmission media, signals propagating through space, radio waves, infrared signals, etc.

In one embodiment, the invention provides for methods of interfacing a software program with a nanomaterial of the invention whereby the nanomaterial is integrated into the pharmaceutical manufacturing process and control of the pharmaceutical manufacturing process is attained. The integration can be used for routine monitoring, quality control, maintenance, hazard mitigation, validation, etc.

In one embodiment, the interface is a combinational logic circuit having and I/O and power supply. In a further embodiment, the interface comprises a chemically assembled electronic nanomaterial having an I/O whereby the nanomaterial is programmed with a logic function. In a further embodiment, the interface comprises a chemically assembled electronic nanomaterial having an I/O whereby the nanomaterial is programmed with a logic function and whereby the nanomaterial is connected to a further nanomaterial via a electronically conductive nanowire whereby the further nanomaterial is programmed with a logic function. One of skill in the art will understand and be enabled to achieve a bottom-up approach to designing the chemically assembled nanomaterial whereby each nanomaterial is linked via nanowires and whereby the top design is the end user (i.e. human) most preferably a member of the pharmaceutical manufacturing quality control unit. One of skill in the art will also appreciate a top-down design to software programming. It is the purpose of the present invention to provide a hybrid approach (i.e. bottom-up and top-down design) to interfacing nanomaterials and software programs that are useful for monitoring and executing the pharmaceutical manufacturing process. (See, FIG. 1).

In one embodiment the nanomaterials are aligned in a linear fashion to create an integrated circuit by forming an array of nanowires on a substrate (nanolayer). In a further embodiment, the nanowires are formed in a two dimensional grid like structure. In one embodiment, the nanomaterials that are interfaced include an input/output (I/O) isolation for power and clock management.

Those of skill in the art will recognize that many modifications may be made without departing from the scope of the present invention.

V.) ANALYSIS

The invention provides for a method of analyzing data that is compiled as a result of the manufacturing of pharmaceuticals. Further the invention provides for the analysis of data that is compiled as a result of a QA program used to monitor the manufacture of drugs in order to maintain the highest level of data integrity. In one embodiment, the parameters of the data will be defined by the quality control unit. Generally, the quality control unit will provide endpoints that need to be achieved to conform to cGMP regulations or in some instances an internal endpoint that is more restrictive to the minimum levels that need to be achieved.

In a preferred embodiment, the invention provides for data analysis using boundary value analysis. The boundary value will be set forth by the quality control unit. Using the boundary values set forth for a particular phase of manufacture the algorithm is defined. Once the algorithm is defined, an algorithm analysis (i.e. logic analysis) takes place. One of skill in the art will appreciate that a wide variety of tools are used to confirm algorithm analysis such as an accuracy study processor.

One of ordinary skill will appreciate that different types of data will require different types of analysis. In a further embodiment, the program provides a method of analyzing block data via a block check. If the block check renders an affirmative analysis, the benchmark has been met and the analysis continues to the next component. If the block check renders a negative the data is flagged via standard recognition files known in the art and a hazard analysis and hazard mitigation occurs.

In a further embodiment, the invention provides for data analysis using branch analysis. The test cases will be set forth by the quality control unit.

In a further embodiment, the invention provides for data analysis using control flow analysis. The control flow analysis will calibrate the design level set forth by the quality control unit which is generated in the design phase.

In a further embodiment, the invention provides for data analysis using failure analysis. The failure analysis is initiated using the failure benchmark set forth by the quality control unit and then using standard techniques to come to error detection. The preferred technique will be top-down. For example, error guessing based on quality control group parameters which are confirmed by error seeding.

In a further embodiment, the invention provides for data analysis using path analysis. The path analysis will be initiated after the design phase and will be used to confirm the design level. On of ordinary skill in the art will appreciate that the path analysis will be a dynamic analysis depending on the complexity of the program modification. For example, the path analysis on the output of an end product will be inherently more complex that the path analysis for the validation of an in-process material. However, one of ordinary skill will understand that the analysis is the same, but the parameters set forth by the quality control unit will differ.

The invention provides for a top-down design to software analysis. This preferred embodiment is advantageous because the parameters of analysis will be fixed for any given process and will be set forth by the quality control unit. Thus, performing software safety code analysis then software safety design analysis, then software safety requirements analysis, and then software safety test analysis will be preferred.

The aforementioned analysis methods are used for several non-limiting embodiments, including but not limited to, validating QA software, validating pharmaceutical manufacturing, and validating process designs wherein the integration of the system design will allow for more efficient determination of acceptance criteria in a batch, in-process material, batch number, control number, and lot number and allow for increased access time thus achieving a more efficient cost-saving manufacturing process.

VI. MANUFACTURING EXECUTION SYSTEMS (MES)

In one embodiment, the interfaced nanomaterial is integrated into a manufacturing execution system that controls the pharmaceutical manufacturing process. It will be understood by one of skill in the art that the computer product integrates the hardware via generally understood devices in the art (i.e. attached to the analog device via an analog to digital converter).

The nanomaterial is integrated into the manufacturing execution system on a device-by-device basis. As previously set forth, the acceptance criteria of all devices used in the drug product manufacture for the purposes of the manufacturing execution system are determined by the quality control unit. The analysis of the pharmaceutical manufacturing occurs using any of the methods disclosed herein. (See FIG. 2). The program monitors and processes the data and stores the data using standard methods. The data is provided to an end user or a plurality of end users for assessing the quality of data generated by the device or devices. Furthermore, the data is stored for comparative analysis to previous batches to provide a risk-based assessment in case of failure. Using the historical analysis will provide a more streamlined pharmaceutical manufacturing process and will monitor to ensure that product quality is maximized. In addition, the invention comprises monitoring the data from initial process, monitoring the data at the end process, and monitoring the data from a routine maintenance schedule to ensure the system maintain data integrity and validation standards predetermined by the quality control unit.

VII.) KITS/ARTICLES OF MANUFACTURE

For use in basic input/output systems, hardware calibrations, software calibrations, computer systems audits, computer system security certification, data validation, different software system analysis, quality control, and the manufacturing of drug products described herein, kits are within the scope of the invention. Such kits can comprise a carrier, package, or container that is compartmentalized to receive one or more containers such as boxes, shrink wrap, and the like, each of the container(s) comprising one of the separate elements to be used in the method, along with a program or insert comprising instructions for use, such as a use described herein.

The kit of the invention will typically comprise the container described above and one or more other containers associated therewith that comprise materials desirable from a commercial and user standpoint, programs listing contents and/or instructions for use, and package inserts with instructions for use.

A program can be present on or with the container. Directions and or other information can also be included on an insert(s) or program(s) which is included with or on the kit. The program can be on or associated with the container.

The terms "kit" and "article of manufacture" can be used as synonyms.

The article of manufacture typically comprises at least one container and at least one program. The containers can be formed from a variety of materials such as glass, metal or plastic.

EXAMPLES

Various aspects of the invention are further described and illustrated by way of the several examples that follow, none of which is intended to limit the scope of the invention.

Example 1

Methods of Interfacing Nanomaterials with Software Program

The nanomaterial or a plurality of nanomaterials disclosed herein are designed via bottom-up design whereby the nanomaterial is designed with a particular functionality. It will be understood by one of skill in the art that the functionality is determined by the pharmaceutical manufacturing process that is being analyzed. The nanomaterial is loaded with an electrical circuit with an I/O interface. Additionally, the software program, computer readable code, and methods disclosed herein are designed by standard methods using a top-down design approach to programming. The software program is interfaced with the functional nanomaterial via the circuit.

The interfaced nanomaterial is used to execute or monitor the pharmaceutical manufacturing process. The nanomaterial is integrated into the pharmaceutical manufacturing system on a device-by-device basis. As previously set forth, the acceptance criteria of all devices used in the drug product manufacture for the purposes of the manufacturing process are determined by the quality control unit. The analysis of the software and hardware occurs using any of the methods disclosed herein. The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined manufacturing approach and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.

The invention further comprises implementation of the nanomaterial and software program described herein into the crystallization process, the tablet press process, the chromatography process, the pH monitoring process, the liquid mixing process, the powder blending process, the water-for-injection systems, the water purification systems, the cell culture systems, and the finishing and packaging systems subset(s) of the pharmaceutical manufacturing process whereby the data compiled by the subset processes is tracked continuously overtime and said data is used to analyze the subset processes and whereby said data is integrated and used to analyze the quality control process of the pharmaceutical manufacturing process at-large. (See FIG. 2).

Example 2

Integration of Software Program into Pharmaceutical Manufacturing Hardware System Utilizing Nanomaterials The nanomaterial or a plurality of nanomaterials disclosed herein are designed via bottom-up design whereby the nanomaterial is designed with a particular functionality. It will be understood by one of skill in the art that the functionality is determined by the pharmaceutical manufacturing process that is being analyzed. The nanomaterial is loaded with an electrical circuit with an I/O interface. Additionally, the software program, computer readable code, and methods disclosed herein are designed by standard methods using a top-down design approach to programming. The software program is interfaced with the functional nanomaterial via the circuit.

The invention comprises the integration of the nanomaterial into a manufacturing hardware system. In this context, the term "hardware" means any physical device used in the pharmaceutical manufacturing process including, but not limited to, blenders, bio-reactors, capping machines, chromatography/separation systems, chilled water/circulating, glycol, coldrooms, clean steam, clean-in-place (CIP), compressed air, D.I./R.O. watersystems, dry heat sterilizers/ovens, fermentation equipment/bio reactors, freezers, filling equipment, filtration/purification, HVAC: environmental controls, incubators/environmentally controlled chambers, labelers, lyophilizers/freeze, dryers, mixing tanks, modular cleanrooms, neutralization systems, plant steam and condensate, process tanks/pressure, vessels, refrigerators, separation/purification equipment, specialty gas, systems, steam generators/pure steam systems, steam sterilizers, stopper washers, solvent recovery systems, tower water systems, waste inactivation systems/"kill" systems, vial inspection systems, vial washers, water for injection (WFI) systems, pure water systems, washers (glass, tank, carboys, etc.).

The interfaced nanomaterial is used to execute or monitor the pharmaceutical manufacturing process. The nanomaterial is integrated into the pharmaceutical manufacturing system on a device-by-device basis. As previously set forth, the acceptance criteria of all devices used in the drug product manufacture for the purposes of the manufacturing process are determined by the quality control unit. The analysis of the software and hardware occurs using any of the methods disclosed herein. The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined manufacturing approach and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.

The invention further comprises implementation of the nanomaterial and software program described herein into the crystallization process, the tablet press process, the chromatography process, the pH monitoring process, the liquid mixing process, the powder blending process, the water-for-injection systems, the water purification systems, the cell culture systems, and the finishing and packaging systems subset(s) of the pharmaceutical manufacturing process whereby the data compiled by the subset processes is tracked continuously overtime and said data is used to analyze the subset processes and whereby said data is integrated and used to analyze the quality control process of the pharmaceutical manufacturing process at-large. (See FIG. 2).

Example 3

Integration of Software Program into Manufacturing Software System Utilizing Nanomaterials The nanomaterial or a plurality of nanomaterials disclosed herein are designed via bottom-up design whereby the nanomaterial is designed with a particular functionality. It will be understood by one of skill in the art that the functionality is determined by the pharmaceutical manufacturing process that is being analyzed. The nanomaterial is loaded with an electrical circuit with an I/O interface. Additionally, the software program, computer readable code, and methods disclosed herein are designed by standard methods using a top-down design approach to programming. The software program is interfaced with the functional nanomaterial via the circuit.

The invention comprises the integration of the computer nanomaterial into a manufacturing software system. In this context, the term "software" means any device used in the pharmaceutical manufacturing process including, but not limited to user-independent audit trails, time-stamped audit trails, data security, confidentiality systems, limited authorized system access, electronic signatures, bar codes, dedicated systems, add-on systems, control files, Internet, LAN's, etc.

The interfaced nanomaterial is used to execute or monitor the pharmaceutical manufacturing process. The nanomaterial is integrated into the pharmaceutical manufacturing system on a device-by-device basis. As previously set forth, the acceptance criteria of all devices used in the drug product manufacture for the purposes of the manufacturing process are determined by the quality control unit. The analysis of the software and hardware occurs using any of the methods disclosed herein. The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined manufacturing approach and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.

The invention further comprises implementation of the nanomaterial and software program described herein into the crystallization process, the tablet press process, the chromatography process, the pH monitoring process, the liquid mixing process, the powder blending process, the water-for-injection systems, the water purification systems, the cell culture systems, and the finishing and packaging systems subset(s) of the pharmaceutical manufacturing process whereby the data compiled by the subset processes is tracked continuously overtime and said data is used to analyze the subset processes and whereby said data is integrated and used to analyze the quality control process of the pharmaceutical manufacturing process at-large. (See FIG. 2).

Example 4

Integration of Software Program and Nanomaterials into a Comprehensive Cost-Saving System The nanomaterial or a plurality of nanomaterials disclosed herein are designed via bottom-up design whereby the nanomaterial is designed with a particular functionality. It will be understood by one of skill in the art that the functionality is determined by the pharmaceutical manufacturing process that is being analyzed. The nanomaterial is loaded with an electrical circuit with an I/O interface. Additionally, the software program, computer readable code, and methods disclosed herein are designed by standard methods using a top-down design approach to programming. The software program is interfaced with the functional nanomaterial via the circuit.

The invention comprises a program and nanomaterial or a plurality of programs and nanomaterials integrated into a comprehensive cost-saving pharmaceutical manufacturing system. A user, preferably a system administrator, logs onto the system via secure means (i.e. password or other security measures known in the art) and inputs the boundary values for a particular component of the drug manufacturing process. The input is at the initial stage, the end product state, or any predetermined interval in between that has been established for routine maintenance by the quality control unit. The data is generated using any one of the various analysis methods described herein (as previously stated the type of analysis used is functional to the device or protocol being monitored or evaluated). Subsequent to the data analysis, any modifications or corrective action to the manufacturing process is implemented. The data is then stored by standard methods known in the art. Scheduled analysis of the stored data is maintained to provide a preventative maintenance of the manufacturing process. Over time, costs are reduced due to the tracking of data and analysis of troubled areas and frequency of hazards that occur on any given device in the manufacturing process. The system is implemented on every device which plays a role in drug manufacturing. The data compiled from every device is analyzed using the methods described herein.

Example 5

Methods of Performing a Membrane Analysis

Crystallization is a key component to the pharmaceutical manufacturing process. Additionally, a substantial number of the pharmaceuticals manufactured today consist of at least one crystallization step. Despite its significance, typical problems consist of unsuitable particle size distribution, impurity issues (incorrect polymorphs, etc.), inconsistent yield, etc.

In one embodiment, the nanomaterial is integrated into the crystallization process system hardware. It will be understood by one of skill in the art that the computer product integrates the hardware via generally understood devices in the art (i.e. attached to the analog device via an analog to digital converter, wireless means, etc.).

The nanomaterial is integrated into the crystallization system on a device-by-device basis. As previously set forth, the acceptance criteria of all devices used in the drug product manufacture for the purposes of the crystallization process are determined by the quality control unit. The nanomaterial monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined crystallization process and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.

The membrane analysis occurs on the crystallization process to determine when membranes are deficient for quality and yield reasons. Using the analysis methods disclosed herein the membrane is replaced upon failure detection. (See FIG. 3).

In one embodiment, the monitoring and analysis of the crystallization systems achieves a step of integration into a manufacturing execution system whereby manufacturing productivity and product quality are increased. Costs are streamlined over time.

Example 6

Methods of Analyzing Surface Deviations

In tablet making, powder is actually compressed together by traditional means. The end results is a pre-set tablet thickness which varies for each particular product. An overload can occur when too much powder is compressed at one time.

In one embodiment, the nanomaterial is integrated into the tablet press system hardware. It will be understood by one of skill in the art that the computer product integrates the hardware via generally understood devices in the art (i.e. attached to the analog device via an analog to digital converter, wireless means, etc.).

The nanomaterial is integrated into the tablet press system on a device-by-device basis. As previously set forth, the acceptance criteria of all devices used in the drug product manufacture for the purposes of the tablet press process are determined by the quality control unit. The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined tablet press process and will monitor to ensure the tablet press set point is not overloaded or underloaded. In addition, the invention comprises monitoring the data from initial process, monitoring the data at the end process, and monitoring the data from a routine maintenance schedule to ensure the system maintain data integrity and validation standard predetermined by the quality control unit.

The nanomaterial analyzes tablets, etc. for surface deviation which could indicate contamination or similarly an out of specification tablet, etc. (See FIG. 4).

In one embodiment, the monitoring and analysis of the tablet press systems achieves a step of integration into a manufacturing execution system whereby manufacturing productivity and product quality are increased. Costs are streamlined over time.

Example 7

Methods of Performing Tribo-Technical Analysis

The nanomaterial is integrated into a pharmaceutical manufacturing system to perform a tribo-technical analysis. It will be understood by one of skill in the art that the computer product integrates the hardware via generally understood devices in the art (i.e. attached to the analog device via an analog to digital converter, wireless means, etc.).

The tribo-technical analysis provides direct three-dimensional visualization of surfaces, measurement of the thickness of solid and liquid lubricants at the nanoscale, measurement of frictional forces at the nanometer scale, surface characterization of morphology, texture, and roughness, and evaluation of mechanical properties such as hardness and elasticity, and plastic deformation at the nanometer scale. The invention further comprises implementation of the tribo-technical analysis into the crystallization process, the tablet press process, the chromatography process, the pH monitoring process, the liquid mixing process, the powder blending process, the water-for-injection systems, the water purification systems, the cell culture systems, and the finishing and packaging systems subset(s) of the pharmaceutical manufacturing process whereby the data compiled by the subset processes is tracked continuously overtime and said data is used to analyze the subset processes and whereby said data is integrated and used to analyze the quality control process of the pharmaceutical manufacturing process at-large.

The nanomaterial analyzes substances, providing a 3-D visualization to characterize morphology, texture, or roughness which could indicate contamination or similarly an out of specification active or passive ingredient. (See FIG. 5).

In one embodiment, the monitoring and tribo-technical analysis achieves a step of integration into a manufacturing execution system whereby manufacturing productivity and product quality are increased. Costs are streamlined over time.

Example 8

Methods of Performing a Porosity/Permeability/Visualization Analysis

The nanomaterial is integrated into a pharmaceutical manufacturing system to perform a porosity, permeability, or visualization analysis. It will be understood by one of skill in the art that the computer product integrates the hardware via generally understood devices in the art (i.e. attached to the analog device via an analog to digital converter, wireless means, etc.).

The porosity and permeability analysis provides for the monitoring of pharmaceutical manufacturing wherein the ingredients can be measured and re-routed within the specific process (i.e. powder blending, liquid-solid filtering, gas-liquid purification, etc). See FIG. 6. The visualization analysis is used to monitor quality parameters such as surface roughness of a final product (i.e. scanning a tablet for cracks or surface deviations outside the quality parameters).

The invention further comprises implementation of the porosity, permeability, and visualization analysis into the crystallization process, the tablet press process, the chromatography process, the pH monitoring process, the liquid mixing process, the powder blending process, the water-for-injection systems, the water purification systems, the cell culture systems, and the finishing and packaging systems subset(s) of the pharmaceutical manufacturing process whereby the data compiled by the subset processes is tracked continuously overtime and said data is used to analyze the subset processes and whereby said data is integrated and used to analyze the quality control process of the pharmaceutical manufacturing process at-large.

In one embodiment, the monitoring and porosity, permeability, and visualization analysis achieves a step of integration into a manufacturing execution system whereby manufacturing productivity and product quality are increased. Costs are streamlined over time.

Example 9

Methods of Interfacing Nanomaterial in Downstream Processing Systems

In the scope of the invention, downstream processing refers to the recovery and purification of biosynthetic products, particularly pharmaceuticals, from natural sources such as animal or plant tissue or fermentation broth, including the recycling of salvageable components and the proper treatment and disposal of waste. It is an essential step in the manufacture of pharmaceuticals such as antibiotics, hormones, antibodies, and vaccines. Downstream processing and analytical bioseparation both refer to the separation or purification of biological products, but at different scales of operation and for different purposes. Downstream processing implies manufacture of a purified product fit for a specific use, generally in marketable quantities, while analytical bioseparation refers to purification for the sole purpose of measuring a component or components of a mixture, and may deal with sample sizes as small as a single cell. It is understood in the art that downstream processing operations are divided into four groups which are applied in order to bring a product from its natural state as a component of a tissue, cell or fermentation broth through progressive improvements in purity and concentration.

Step 1: Removal of Insolubles

This first step and involves the capture of the product as a solute in a particulate-free liquid, for example the separation of cells, cell debris, or other particulate matter from fermentation broth containing an antibiotic. Typical operations to achieve this are filtration, centrifugation, sedimentation, flocculation, electro-precipitation, and gravity settling. Additional operations such as grinding, homogenization, or leaching, required to recover products from solid sources such as plant and animal tissues, are usually included in this group. The nanomaterial is integrated into step 1 according to the present invention.

Step 2: Product Isolation

The second step is removal of those components whose properties vary substantially from that of the desired product. Generally, water is the chief impurity and isolation steps are designed to remove most of it, reducing the volume of material to be handled and concentrating the product. Solvent extraction, adsorption, ultrafiltration, and precipitation are some of the operations involved. The nanomaterial is integrated into step 2 according to the present invention.

Step 3: Product Purification

The third step is done to separate those contaminants that resemble the product very closely in physical and chemical properties. The nanomaterials of the present invention are utilized heavily in step 3 due to the ability to deliver precise measurements at the nanoscale. This stage contributes a significant fraction of the entire downstream processing expenditure in terms of cost. Examples of operations include affinity, size exclusion and reversed phase chromatography, crystallization, and fractional precipitation. The nanomaterial is integrated into step 3 according to the present invention.

Step 4: Product Polishing

The final processing step which ends with packaging of the product in a form that is stable, easily transportable and convenient. Crystallization, desiccation, lyophilization and spray drying are typical operations. Depending on the product and its intended use, polishing may also include operations to sterilize the product and remove or deactivate trace contaminants which might compromise product safety. Such operations might include the removal of viruses or depyrogenation. The nanomaterial is integrated into step 4 according to the present invention. The nanomaterial or a plurality of nanomaterials disclosed herein are designed via bottom-up design whereby the nanomaterial is designed with a particular functionality. It will be understood by one of skill in the art that the functionality is determined by the pharmaceutical manufacturing process that is being analyzed. The nanomaterial is loaded with an electrical circuit with an I/O interface. Additionally, the software program, computer readable code, and methods disclosed herein are designed by standard methods using a top-down design approach to programming. The software program is interfaced with the functional nanomaterial via the circuit.

The interfaced nanomaterial is used to execute or monitor a downstream process. (See FIG. 7).

In one embodiment, the integration of the nanomaterial into a downstream process achieves a step of integration into a manufacturing execution system whereby manufacturing productivity and product quality are increased. Costs are streamlined over time.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A system comprising:
    an electronic circuit;
    a filter membrane; and
    an optically enhanced nanomaterial adapted to scan the filter membrane, said an optically enhanced nanomaterial operably linked to said electronic circuit, whereby the electronic circuit is programmed with a logic function and whereby said logic function is interfaced with a computer memory having computer executable instructions to continuously monitor data generating by scanning the filter membrane with the optically enhanced nanomaterial during a pharmaceutical crystallization manufacturing process and to analyze the data for determination of quality or yield parameters against a predetermined quality or yield parameter.

2. The system of claim 1, wherein the nanomaterial is selected from the group consisting of a nanocomposite, nanocrystal, and nanopowder.

3. The system of claim 1, wherein the electronic circuit is a combinational logic circuit having an I/O function and a power supply.

4. The system of claim 1, wherein the nanomaterial is chemically assembled.

5. The system of claim 1, wherein the nanomaterial is designed via a bottom-up design.

6. A kit comprising the system of claim 1.

7. A method of interfacing the system of claim 1 with a pharmaceutical manufacturing process said method comprising,
    a) contacting said system to a device used in a pharmaceutical manufacturing process wherein said system monitors a critical control point;
    b) monitoring data generated by said system during pharmaceutical manufacture;
    c) analyzing the data to determine if the critical control point has an adverse effect on a finished pharmaceutical.

8. The method of claim 7, wherein said system comprises an is optically enhanced nanomaterial.

9. The method of claim 7, wherein the device is a pharmaceutical manufacturing software system selected from the group consisting of user-independent audit trails, time-stamped audit trails, data security, confidentiality systems, limited authorized system access, electronic signatures, bar codes, dedicated systems, add-on systems, control files, Internet, and LAN's.

10. The method of claim 7, wherein the device is a tablet press or powder blending device.

11. The method of claim 7, wherein the pharmaceutical manufacturing process is selected from the group consisting of crystallization, product isolation, product purification, product polishing, and chromatography.

12. The method of claim 7, wherein the data is generated during production of an active ingredient.

* * * * *